(12) United States Patent
Ferrari et al.

(10) Patent No.: US 7,820,146 B2
(45) Date of Patent: *Oct. 26, 2010

(54) CARE AND/OR MAKE-UP COSMETIC COMPOSITION STRUCTURED WITH SILICONE POLYMERS AND ORGANOGELLING AGENTS, IN RIGID FORM

(75) Inventors: Véronique Ferrari, Maisons-Alfort (FR); Jean Mondet, Aulnay-sous-Bois (FR)

(73) Assignee: L'Oreal S.A., Paris (FR)

( * ) Notice: Subject to any disclaimer, the term of this patent is extended or adjusted under 35 U.S.C. 154(b) by 235 days.

This patent is subject to a terminal disclaimer.

(21) Appl. No.: 10/517,390

(22) PCT Filed: Jun. 2, 2003

(86) PCT No.: PCT/EP03/06463

§ 371 (c)(1), (2), (4) Date: Dec. 10, 2004

(87) PCT Pub. No.: WO03/105788

PCT Pub. Date: Dec. 24, 2003

(65) Prior Publication Data

US 2005/0245673 A1 Nov. 3, 2005

Related U.S. Application Data

(60) Provisional application No. 60/391,617, filed on Jun. 27, 2002.

(30) Foreign Application Priority Data

Jun. 12, 2002 (FR) .................................. 02 07206

(51) Int. Cl.
*A61K 8/89* (2006.01)
(52) U.S. Cl. ............................ 424/63; 424/64; 424/401
(58) Field of Classification Search .................. 424/63, 424/64, 401
See application file for complete search history.

(56) References Cited

U.S. PATENT DOCUMENTS

| | | | |
|---|---|---|---|
| 2,823,195 A | 2/1958 | Shorr et al. | |
| 2,823,218 A | 2/1958 | Speler et al. | |
| 3,723,566 A | 3/1973 | Thompson et al. | |
| 4,322,400 A | 3/1982 | Yuhas | |
| 4,822,852 A | 4/1989 | Wittmann et al. | |
| 5,262,505 A | 11/1993 | Nakashima et al. | |
| 5,407,986 A | 4/1995 | Furukawa et al. | |
| 5,412,004 A | 5/1995 | Tachibana et al. | |
| 5,473,041 A | 12/1995 | Itoh | |
| 5,512,272 A | 4/1996 | Krzysik | |
| 5,567,428 A | 10/1996 | Hughes | |
| 5,725,882 A | 3/1998 | Kumar et al. | |
| 5,837,223 A | 11/1998 | Barone et al. | |
| 5,874,069 A | 2/1999 | Mendolia et al. | |
| 5,919,441 A | 7/1999 | Mendolia et al. | |
| 5,969,172 A | 10/1999 | Nye | |
| 5,981,680 A | 11/1999 | Petroff et al. | |
| 5,985,297 A | 11/1999 | Mellul et al. | |
| 6,045,782 A | 4/2000 | Krog et al. | |
| 6,051,216 A | 4/2000 | Barr et al. | |
| 6,060,072 A | 5/2000 | Konik et al. | |
| 6,103,250 A | 8/2000 | Brieva et al. | |
| 6,177,091 B1 | 1/2001 | Bara et al. | |
| 6,353,076 B1 | 3/2002 | Barr et al. | |
| 6,362,287 B1 | 3/2002 | Chorvath et al. | |
| 6,362,288 B1 | 3/2002 | Brewer et al. | |
| 6,372,235 B1 | 4/2002 | Livoreil et al. | |
| 6,376,078 B1 | 4/2002 | Inokuchi | |
| 6,423,324 B1 | 7/2002 | Murphy et al. | |
| 6,426,062 B1 | 7/2002 | Chopra et al. | |
| 6,451,295 B1 * | 9/2002 | Cai et al. ..................... | 424/65 |
| 6,503,632 B1 | 1/2003 | Hayashi et al. | |
| 6,524,598 B2 | 2/2003 | Sunkel et al. | |
| 6,541,017 B1 | 4/2003 | Lemann et al. | |
| 6,569,955 B1 | 5/2003 | Brewer et al. | |

(Continued)

FOREIGN PATENT DOCUMENTS

EP 0 377 447 A2 7/1990

(Continued)

OTHER PUBLICATIONS

U.S. Appl. No. 11/342,748, filed Jan. 31, 2006, Blin, et al.
U.S. Appl. No. 11/254,919, filed Oct. 21, 2005, Lu, et al.
Dow Corning® 2-8178 Gellant, Ref. No. 27-1055-01, Aug. 2002, 35 pp.
Dow Corning® 2-8178 Gellant, Product Information Personal Care, 6 pp.
Shin-Etsu Silicones for Personal Care; Product Brochure, KSP-100•101•102•103•104•105 "Hybrid Silicone Powders for Personal Care".
Shin-Etsu Silicones for Personal Care; Product Brochure, KSP-200•300 "Hybrid Silicone Powders containing Fluoroalkyl or Phenyl group for Personal Care".
English Language Derwent Abstract of EP 0 923 928, Jun. 23, 1999.

(Continued)

*Primary Examiner*—Margaret G Moore
(74) *Attorney, Agent, or Firm*—Oblon, Spivak, McClelland, Maier & Neustadt, L.L.P.

(57) ABSTRACT

The invention relates to a care and/or make-up cosmetic composition comprising a liquid fatty phase comprising at least one silicone oil, structured with a gelling system comprising 1) at least one polymer having a weight-average molecular mass ranging from 500 to 500 000, containing at least one moiety comprising:
at least one polyorganosiloxane group consisting of 1 to 1 000 organosiloxane units in the chain of the moiety or in the form of a graft, and
at least two groups capable of establishing hydrogen interactions,
the polymer being solid at room temperature and soluble in the liquid fatty phase at a temperature of 25 to 250° C., and 2) at least one non-polymeric organogelling agent.

42 Claims, No Drawings

U.S. PATENT DOCUMENTS

| | | |
|---|---|---|
| 6,682,748 B1 | 1/2004 | De La Poterie et al. |
| 6,916,464 B2 | 7/2005 | Hansenne et al. |
| 7,288,262 B1 | 10/2007 | Livoreil |
| 2001/0051171 A1 | 12/2001 | Mondet |
| 2001/0053377 A1 | 12/2001 | Monet et al. |
| 2002/0028223 A1 | 3/2002 | Vatter et al. |
| 2002/0048557 A1 | 4/2002 | Cai et al. |
| 2002/0051758 A1 | 5/2002 | Cai et al. |
| 2002/0150602 A1 | 10/2002 | Livoreil et al. |
| 2003/0068348 A1 | 4/2003 | Ferrari et al. |
| 2003/0072730 A1 | 4/2003 | Tournilhac |
| 2003/0082129 A1 | 5/2003 | Buckingham et al. |
| 2003/0170188 A1 | 9/2003 | Ferrari et al. |
| 2003/0228333 A1 | 12/2003 | Fecht et al. |
| 2003/0232030 A1 | 12/2003 | Lu et al. |
| 2003/0235548 A1 | 12/2003 | Lu et al. |
| 2003/0235552 A1 | 12/2003 | Yu |
| 2003/0235553 A1 | 12/2003 | Lu et al. |
| 2004/0001799 A1 | 1/2004 | Lu et al. |
| 2004/0115153 A1 | 6/2004 | Yu |
| 2004/0115154 A1 | 6/2004 | Yu |
| 2004/0120912 A1 | 6/2004 | Yu |
| 2004/0126336 A1 | 7/2004 | Hansenne et al. |
| 2004/0170586 A1 | 9/2004 | Ferrari et al. |
| 2004/0180032 A1 | 9/2004 | Manelski et al. |
| 2004/0197285 A1 | 10/2004 | Van Dort |
| 2004/0223936 A1 | 11/2004 | Fecht et al. |
| 2005/0009989 A1 | 1/2005 | Liew et al. |
| 2005/0020769 A1 | 1/2005 | Lu et al. |
| 2005/0089492 A1 | 4/2005 | Lu et al. |
| 2005/0158260 A1 | 7/2005 | Ferrari et al. |
| 2008/0171008 A1 | 7/2008 | Bui |

FOREIGN PATENT DOCUMENTS

| | | |
|---|---|---|
| EP | 0 594 285 A2 | 4/1994 |
| EP | 0 693 517 A1 | 1/1996 |
| EP | 0 709083 | 5/1996 |
| EP | 0 923 928 | 6/1999 |
| EP | 1 048 686 | 11/2000 |
| EP | 1 068 856 | 1/2001 |
| EP | 1 266 647 | 12/2002 |
| EP | 1 266 648 | 12/2002 |
| FR | 2 765 800 | 1/1999 |
| GB | 134 8783 | 3/1974 |
| JP | 02-25411 | 1/1990 |
| JP | 06-279253 | 10/1994 |
| JP | 08-239316 | 10/1994 |
| JP | H7-138555 | 5/1995 |
| JP | 09-071505 | 3/1997 |
| JP | H10-237034 | 9/1998 |
| JP | 11-236314 | 8/1999 |
| JP | 2000-38450 | 2/2000 |
| JP | 2001-58915 | 3/2001 |
| JP | 2001-081009 | 3/2001 |
| JP | 2001-503070 | 3/2001 |
| JP | 2001-114630 | 4/2001 |
| JP | 2001-512164 | 8/2001 |
| JP | 2001-316244 | 11/2001 |
| JP | 2002-12514 | 1/2002 |
| WO | WO 97/36572 | 10/1997 |
| WO | WO 97/36573 | 10/1997 |
| WO | WO 99/47111 | 1/1999 |
| WO | WO 99/06473 | 2/1999 |
| WO | WO 99/21528 | 5/1999 |
| WO | WO99/22710 | 5/1999 |
| WO | WO 01/09239 A1 | 2/2001 |
| WO | WO 01/97758 A2 | 12/2001 |
| WO | WO 02/05763 | 1/2002 |
| WO | WO 02/17870 A2 | 3/2002 |
| WO | WO 02/17871 A2 | 3/2002 |
| WO | WO 02/089760 A1 | 11/2002 |
| WO | WO 03/013447 A2 | 2/2003 |
| WO | WO 03/105788 A2 | 6/2003 |
| WO | WO 03/101412 A2 | 12/2003 |
| WO | WO 2004/054523 | 7/2004 |
| WO | WO 2004/054524 | 7/2004 |

OTHER PUBLICATIONS

English Language Derwent Abstract of EP 1 068 856, Jan. 17, 2001.
English Language Derwent Abstract of FR 2 765 800, Jan. 15, 1999.
U.S. Appl. No. 10/538,920, filed Jun. 13, 2005, Blin, et al.
U.S. Appl. No. 10/538,924, filed Jun. 13, 2005, Tournilhac, et al.
U.S. Appl. No. 11/193,444, filed Aug. 1, 2005, Chen, et al.
U.S. Appl. No. 11/024,471, filed Dec. 30, 2004, Blin, et al.
U.S. Appl. No. 11/217,293, filed Sep. 2, 2005, Bui, et al.
U.S. Appl. No. 12/648,020, filed Dec. 28, 2009, Yu.
U.S. Appl. No. 11/898,093, filed Sep. 10, 2007, Ferrari, et al.
Dow Corning 2-8178 Gellant, Ref. No. 27-1055B-01, Apr. 16, 2003, 6 pp.

* cited by examiner

CARE AND/OR MAKE-UP COSMETIC COMPOSITION STRUCTURED WITH SILICONE POLYMERS AND ORGANOGELLING AGENTS, IN RIGID FORM

CROSS REFERENCE TO RELATED APPLICATIONS

This application is a National Phase Application based on PCT/EP03/06463, filed on Jun. 2, 2003, which claims the priority of French Application No. 0207206, filed on Jun. 12, 2002, and the benefit of U.S. Provisional Application No. 60/391,617, filed on Jun. 27, 2002, the contents of all of which are incorporated herein by reference.

TECHNICAL FIELD

The present invention relates to a care and/or treatment and/or make-up cosmetic composition for the skin, including the scalp, and/or the lips of human beings, containing a liquid fatty phase comprising at least one silicone oil, gelled with a particular polymer, provided in particular in the form of a cast make-up product, in particular as a make-up stick such as lipsticks, whose application leads to a glossy and non-migrating deposit.

A care and/or treatment cosmetic composition is a composition which comprises at least one active compound for treating wrinkles, for moisturizing the skin and the lips, for protecting the skin, the lips and superficial body growths from ultraviolet rays, for treating acne and/or for acting as self-tanning agent.

The invention relates more particularly to cosmetic and dermatological compositions such as make-up products exhibiting properties of staying power, non-transfer and stability.

PRIOR STATE OF THE ART

In cosmetic or dermatological products, it is common to find a structured, namely gelled and/or rigidified, liquid fatty phase; this is in particular the case in solid compositions such as deodorants, balms and lipsticks, eyeshadows, concealer products and foundations which have been cast. This structuring is obtained with the aid of waxes or fillers. Unfortunately, these waxes and fillers tend to mattify the composition, which is not always desirable in particular for a lipstick or an eyeshadow.

The expression liquid fatty phase is understood to mean, for the purposes of the application, a fatty phase which is liquid at room temperature (25° C.) and atmospheric pressure (760 mmHg), which is composed of one or more fatty substances which are liquid at room temperature, which are also called oils, which are compatible with each other and which contain a silicone oil.

The expression structured liquid fatty phase is understood to mean, for the purposes of the application, that this structured phase does not run under its own weight.

The structuring of the liquid fatty phase makes it possible in particular to limit its exudation from solid compositions and, furthermore, to limit, after deposition on the skin or the lips, the migration of this phase into wrinkles and fine lines, which is particularly sought for a lipstick or an eyeshadow. Indeed, substantial migration of the liquid fatty phase, charged with colouring matter, leads to an inaesthetic effect around the lips or the eyes, particularly accentuating the wrinkles and fine lines. This migration is often cited by women as a major defect of conventional lipsticks or eyeshadows. The expression migration is understood to mean an overflowing of the composition deposited on the skin or the lips, outside its initial outline.

The gloss is mainly linked to the nature of the liquid fatty phase. Thus, it is possible to reduce the amount of waxes and fillers in the composition in order to increase the gloss of a lipstick, but then the migration of the liquid fatty phase increases. In other words, the amounts of waxes and fillers necessary for producing a stick of suitable hardness are a barrier to the gloss of the deposit.

The document EP-A-1 068 856 [1] describes solid cosmetic compositions, with no wax, containing a liquid fatty phase structured with a polymer, in which the fatty phase is mainly a non-silicone oil.

The document WO-A-01/97758 [2] describes cosmetic compositions based on polyamide resins comprising a gelling agent chosen from esters and amides of N-acylamino acids and mixtures thereof. The composition also comprises a solvent for the polyamide resin which may be chosen from unsaturated and saturated fatty alcohols, fatty and/or aromatic carboxylic acid esters, ethoxylated and/or propoxylated alcohols and acids, silicones, mineral oils and branched-chain hydrocarbons; preferably, fatty acid esters, fatty alcohols, mineral oils, branched hydrocarbons and mixtures thereof.

The use of fatty phases based on silicone oils makes it possible currently to obtain cosmetic compositions having a long staying power when the oils are only slightly volatile or are non-volatile, namely a good staying power in particular of the colour over time (unchanging, unfading), and transfer-free compositions when the silicone oils are volatile, not forming a deposit on a support such as a glass, a cup, a fabric or a cigarette, placed in contact with the film of make-up.

Currently, the use of silicone oils in cosmetics is limited by the small number of molecules which can gel these media and thus give compositions which exist in solid form such as lipsticks or cast foundations for example. The use of cosmetic compositions whose fatty phase is predominantly siliconized leads, in most cases, to problems of compatibility with the ingredients conventionally used in cosmetics.

In the documents U.S. Pat. No. 5,874,069 [3], U.S. Pat. No. 5,919,441 [4], U.S. Pat. No. 6,051,216 [5], WO-A-99/06473 [40], U.S. Pat. No. 6,353,076 [41], WO-A-02/17870 [6], and WO-A-02/17871 [7], cosmetic compositions such as deodorant sticks or gels, comprising a silicone oily phase gelled with a polysiloxane- and polyamide-based wax, or with a polymer containing siloxane groups and groups capable of hydrogen interactions, have been prepared.

In WO-A-02/17870 [6], it is envisaged to add to the composition another gelling agent, but the quantities added should be low, for example less than 0.5% in the case of hydroxystearic acid, in order to preserve the clarity of the product.

In WO-A-02/17871 [7], it is also envisaged to use a second gelling agent with the silicone polymer in a quantity representing 0.5 to 2% by weight of the composition, and a solvent system comprising a non-silicone organic compound, a volatile silicone and optionally another silicone.

The document EP-A-1 177 784 [8] illustrates a deodorant composition comprising a liquid phase containing, for example, a volatile silicone and optionally a non-volatile silicone and/or a non-silicone hydrophobic organic liquid, structured with an organic compound with amido groups, with optionally one or more polymeric or non-polymeric secondary structuring agents in small proportions. Among the secondary structuring agents, this document mentions polymers having siloxane groups and groups exhibiting hydrogen interactions without giving examples or results on a composition using these polymers.

It should be stated that the documents [6], [7] and [8] relate to deodorants for which the problems of exudation and migration of the liquid fatty phase charged with colouring matter into wrinkles and fine lines, and of staying power and non-transfer of the composition, do not exist as in the case of the make-up cosmetic products described above. Moreover, no gloss is sought for deodorants.

In addition, the sticks obtained by structuring the liquid fatty phase with solely one or more gelling silicone polymers do not exhibit sufficient mechanical resistance to shearing, in particular during the application of the stick to the lips and/or the skin, leading to breaking of the stick.

DISCLOSURE OF THE INVENTION

The subject of the invention is precisely a care and/or make-up and/or treatment composition for the skin and/or the lips, which makes it possible to overcome the disadvantages mentioned above.

Surprisingly, the applicant has found that the use of particular polymers combined with one or more non-polymeric organogelling agents made it possible to structure, in the absence or in the presence of small quantities of wax, the silicone oil-based liquid fatty phases, in the form of a make-up or care product whose application led to a glossy, satiny or matt film according to the wishes of the user and/or the type of non-migrating product desired, and to reinforce the staying power and/or transfer-free properties of these products. In addition, their heat-stability is enhanced.

The expression stable is understood to mean a composition which does not exude at room temperature (25° C.) for at least 2 months, or even up to 9 months.

The combination of these polymers with one or more organogelling agents makes it possible to obtain gels, in particular solid gels, having a good mechanical strength and an acceptable rheology in order to allow a deposit in a sufficient quantity which does not feel sticky, which has a very good staying power, which is transfer-free (in particular when volatile silicone oils are used) and which does not migrate into wrinkles and fine lines.

The effects obtained by virtue of this combination do not appear in the documents relating to deodorants which possibly envisage this combination since the problems solved by this combination do not exist in the field of deodorants.

The invention not only applies to make-up products for the lips such as lipsticks, lip pencils and lip glosses, but also to care and/or treatment products for the skin, including the scalp, and the lips, such as sun protection products in stick form for the skin, the face or the lips, or lip balms, to make-up products for the skin, both of the face and of the human body, such as foundations cast as a stick or in a dish, concealer products and temporary tattoo products, to cleansing products, in particular in stick form, and to make-up products for the eyes such as eyeliners, in particular in pencil form, and mascaras, in particular cakes for keratinous fibres (eyelashes, eyebrows, hair).

More precisely, the subject of the invention is a care and/or make-up cosmetic composition comprising a liquid fatty phase comprising at least one silicone oil, structured with at least one gelling system comprising a) at least one polymer (homopolymer or copolymer) having a weight-average molecular mass ranging from 500 to 500 000, containing at least one moiety comprising:

at least one polyorganosiloxane group consisting of 1 to 1 000 organosiloxane units in the chain of the moiety or in the form of a graft, and at least two groups capable of establishing hydrogen interactions, chosen from ester, amide, sulphonamide, carbamate, thiocarbamate, urea, thiourea, oxamido, guanidino and biguanidino groups, and combinations thereof, provided that at least one of the groups is different from an ester group, and b) at least one non-polymeric organogelling agent, the liquid fatty phase and the gelling system forming a physiologically acceptable medium.

According to the invention, the expression "gelling system" is understood to mean a system which makes it possible to rigidify the composition by forming hydrogen bonds.

The composition of the invention may be provided in the form of a paste, a solid or a more or less viscous cream. It may be a simple or multiple, in particular an oil-in-water or a water-in-oil, emulsion, a rigid or soft gel having an oily continuous phase. The simple or multiple emulsion may comprise an aqueous or oily continuous phase optionally containing dispersed lipid vesicles. In particular, it is provided in a form cast as a stick or in a dish and more especially in the form of an oily, in particular anhydrous, rigid gel and in particular of an anhydrous stick. More especially, it is provided in the form of a translucent or opaque rigid gel (according to whether it contains pigments or otherwise), the liquid fatty phase forming the continuous phase. An anhydrous composition will comprise less than 10% by weight of water, for example less than 5% by weight.

The structuring of the liquid fatty phase can be modulated according to the nature of the polymer and the non-polymeric organogelling agent used in the gelling system, and may be such that a rigid structure is obtained in the form of a baton or a stick, having good mechanical strength. When they are coloured, these batons make it possible, after application, to obtain a glossy deposit, which does not migrate and which has good staying power, in particular of the colour over time. The composition may comprise one or more structuring polymers and one or more non-polymeric organogelling agents.

Advantageously, the composition of the invention is a composition for the lips and even better a lipstick composition in particular in stick form.

Liquid Fatty Phase

According to the invention, the liquid fatty phase comprises at least one silicone oil which may be a volatile oil, a non-volatile oil or a mixture of volatile oil(s) and of non-volatile oil(s). An oil is a non-aqueous compound which is immiscible with water.

According to the invention, the volatile silicone oil may be chosen from linear or cyclic silicone oils having a flash point equal to or greater than 40° C. and advantageously greater than the softening point of the gelling system and/or a viscosity of less than 8 cSt, such as linear or cyclic polydimethylsiloxanes (PDMS) having from 3 to 7 silicon atoms.

By way of examples of such volatile oils, there may be mentioned the compounds given in Table 1 below.

The non-volatile silicone oils may be polydimethylsiloxanes, polyalkylmethylsiloxanes, dimethicone copolyols, alkylmethicone copolyols, cetyldimethicone, silicones with alkylglyceryl ether groups, silicones with side amine groups and dilauroyltrimethylol propane siloxysilicate. The alkyl groups of these oils have in particular from 2 to 24 carbon atoms.

The non-volatile silicone oils which can be used in the invention may be in particular linear, non-volatile polydimethylsiloxanes (PDMS) which are liquid at room temperature; polydimethylsiloxanes containing alkyl, alkoxy or phenyl groups, which are pendent and/or at the silicone chain end, groups each having from 2 to 24 carbon atoms; phenylated silicones such as phenyltrimethicones, phenyldimethicones, phenyltrimethylsiloxy diphenylsiloxanes, diphenyldimethicones, diphenylmethyldiphenyltrisiloxanes, 2-phenylethyl trimethylsiloxysilicates, fluorinated silicones with one or more group(s) that is (are) pendent or at the chain end having from 1 to 12 carbon atoms of which all or some of the hydrogen atoms are substituted with fluorine atoms, dimethiconols and mixtures thereof.

According to the invention, the liquid fatty phase may comprise at least one volatile silicone oil and at least one volatile non-silicone oil.

For the purposes of the invention, a volatile silicone or non-silicone oil has a flash point preferably of 40 to 135° C. or no flash point. Volatile oils have at room temperature (25° C.) and atmospheric pressure (760 mmHg) a vapour pressure ranging from 0.02 mm to 300 mmHg (2.66 Pa to 40 000 Pa) and even better ranging from 0.1 to 90 mmHg (13 Pa to 12 000 Pa). The non-volatile oils then correspond to a vapour pressure of less than 0.02 mmHg (2.66 Pa).

The silicone oils of the invention have a viscosity which is advantageously chosen from the ranging going from 5 to 800 000 cSt at 25° C., preferably from 10 to 500 000 cSt, and even better from 10 to 5 000 cSt.

TABLE 1

| Compound | Flash point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF 96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 cSt |
| PDMS DC 200 (3 cSt) from Dow Corning | 102 | 3 cSt |

The volatile silicone oil may also be chosen from the group comprising fluorinated silicone oils such as silicones with alkyl and perfluoroalkyl groups, silicones with oxyethylenated/oxypropylenated (EO/PP) side groups and with perfluorinated groups, silicones with perfluorinated side groups and with glycerolated side groups, perfluoroalkylmethylphenylsiloxanes, these oils having a vapour pressure greater than or equal to 0.02 mmHg.

According to the invention, the liquid fatty phase may contain one or more volatile or non-volatile non-silicone oils. The volatile non-silicone oils may be chosen from the group comprising hydrocarbon oils and volatile esters and ethers such as volatile hydrocarbons such as isododecane and isohexadecane, $C_8$-$C_{16}$ isoparaffins, isohexyl or isodecyl neopentanoates.

The volatile non-silicone oil may also be chosen from fluorinated oils such as perfluoropolyethers, perfluoroalkanes such as perfluorodecalin, perfluorodamantanes, monoesters, diesters and triesters of perfluoroalkyl phosphates and fluorinated ester oils.

By way of example of volatile non-silicone oils which can be used in the invention, there may be mentioned the compounds of Table 2 which follows.

TABLE 2

| Compound | Flash point (° C.) |
| --- | --- |
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methyl ether acetate* | 46 |
| Isopar L ($C_{11}$-$C_{13}$ isoparaffin) | 62 |
| Isopar H ($C_{11}$-$C_{12}$ isoparaffin) | 56 |

The liquid fatty phase advantageously contains at least 30%, and even better at least 40% by weight of silicone oil(s) advantageously having a viscosity of less than 1 000 cSt and even better of less than 100 cSt because the silicone polymers used in the invention are more soluble in silicone oils of low viscosity. It may also contain other non-silicone oils or a mixture of non-silicone oils.

When the fatty phase comprises a volatile oil, it advantageously represents from 3 to 89.4%, and even better from 5 to 60%, for example from 5 to 10% of the total weight of the composition.

The liquid fatty phase may also contain other non-silicone oils, for example polar oils such as:

hydrocarbonaceous vegetable oils with a high content of triglycerides consisting of esters of fatty acids and of glycerol in which the fatty acids may have varied chain lengths, it being possible for the latter to be linear or branched, saturated or unsaturated; these oils are in particular wheat germ, maize, sunflower, karite, castor, sweet almond, macadamia, apricot, soybean, rapeseed, cottonseed, lucerne, poppy seed, pumpkin seed, sesame, gourd, avocado, hazelnut, grapeseed or blackcurrant seed, evening primrose, millet, barley, quinoa, olive, rye, safflower, candlenut, passion flower and rose musk oils; or triglycerides of caprylic/capric acids such as those sold by the company Stearines Dubois or those sold under the names Miglyol 810, 812 and 818 by the company Dynamit Nobel;

synthetic oils or esters of formula $R_5COOR_6$ in which $R_5$ represents the residue of a linear or branched higher fatty acid containing from 1 to 40 and even better from 7 to 19 carbon atoms and $R_6$ represents a branched hydrocarbon chain containing from 1 to 40 and even better from 3 to 20 carbon atoms, with $R_5+R_6 \geq 10$ such as, for example, Purcellin oil (ketostearyl octanoate), isononyl isononanoate, $C_{12}$ to $C_{15}$ alcohol benzoate, isopropyl myristate, 2-ethylhexyl palmitate, octanoates, decanoates or ricinoleates of alcohols or of polyalcohols; hydroxylated esters such as isostearyl lactate, diisostearyl malate; and esters of pentaerythritol;

synthetic esters having from 10 to 40 carbon atoms;

$C_8$ to $C_{26}$ fatty alcohols such as oleyl alcohol and octyldodecanol;

fatty acids such as oleic, linoleic or linolenic acid; and mixtures thereof.

The liquid fatty phase may also contain apolar oils such as linear or branched hydrocarbons or fluorocarbons of synthetic or mineral origin, which are volatile or not, such as volatile oils of paraffin (such as isoparaffins, isododecane) or non-volatile oils of paraffin and its derivatives, petroleum jelly, polydecenes, hydrogenated polyisobutene such as parleam, squalane, and mixtures thereof.

Generally, the liquid fatty phase represents from 5 to 99% of the total weight of the composition and even better from 20 to 75%.

Solid Particles

According to the invention, the composition generally comprises, in addition, solid particles chosen from fillers and pigments. Generally, the mean size of the solid particles is from 10 nm to 50 µm, and even better from 50 nm to 30 µm, for example from 100 nm to 10 µm.

The fillers used in the cosmetic compositions are generally intended to absorb sweat and sebum and/or to provide mattness. According to the invention, they further make it possible to structure the liquid fatty phase containing a silicone oil and to reinforce the staying power and/or transfer-free properties of the composition and also the heat stability.

The expression pigments is understood to mean any solid particle insoluble in the composition which serves to give and/or modify a colour and/or an iridescent appearance.

These pigments may simultaneously provide the function of absorption of sweat and of sebum, and the function of coloration or of modification of appearance of the composition, that is of the make-up and/or care cosmetic product. In the invention, they also bring about the structuring of the liquid fatty phase.

These fillers or pigments may be either of a hydrophobic nature, or of a hydrophilic nature. When these fillers or pigments are hydrophilic particles, their dispersion in the composition is facilitated either by coating them with a film of hydrophobic compound or by adding a dispersant and in particular an amphiphilic silicone to the composition.

The hydrophobic pigments or fillers may consist of hydrophobic polymer or copolymer powders. By way of example of hydrophobic polymers and copolymers used as fillers, there may be mentioned:

1) fluorinated polymers such as polytetrafluoroethylene powders and tetrafluoroethylene and olefin, for example ethylene or propylene, copolymer powders; 2) silicone elastomers, for example polymethylsilsesquioxane powders (Tospearl® from Toshiba); 3) polyolefins such as polyethylene; 4) polyalkyl methacrylates, for example polymethyl methacrylate; 5) polyamides (Nylon®); 6) polystyrenes; 7) polyesters and derivatives thereof; 8) polyacrylics (Polytrap® from Dow Corning) or polymethyl methacrylate; and 9) polyurethanes, for example hexamethylene diisocyanate/trimethylol hexalactone powders.

It is also possible to use hydrophilic fillers which are surface-treated so as to be hydrophobic, such as boron nitride, starch, precipitated calcium carbonate, silica, glass, or a ceramic.

Instead of powders, it is of course possible to use fibres of a hydrophobic nature, in particular fibres of the polymers and copolymers mentioned above.

The solid particles may also consist of pigments and/or pearlescent agents which make it possible to obtain a make-up with high coverage, that is to say which does not reveal the skin, the lips or the superficial body growths. These particles make it possible, in addition, to reduce the sticky feel of the compositions.

The pigments may be white or coloured, inorganic and/or organic, coated or not. There may be mentioned, among the inorganic pigments, titanium or zinc dioxide, optionally surface-treated, zirconium or cerium oxides, and iron or chromium oxides, manganese violet, ultramarine blue, chromium hydrate and ferric blue. Among the organic pigments, there may be mentioned carbon black, pigments of the D & C type, and lacquers based on carmine, barium, strontium, calcium or aluminium. The pigments may represent from 0.1 to 50%, preferably from 0.5 to 40%, and even better from 2 to 30% of the total weight of the composition.

The pearlescent pigments (or pearlescent agents) may be chosen from white pearlescent pigments such as mica coated with titanium, or with bismuth oxychloride, coloured pearlescent pigments such as mica-titanium with iron oxides, mica-titanium with in particular ferric blue and chromium oxide, mica-titanium with an organic pigment of the above-mentioned type and pearlescent pigments based on bismuth oxychloride. The pearlescent pigments may also have goniochromatic properties and may be provided in the form of liquid crystals or multilayer platelets. They may represent from 0 to 30% of the total weight of the composition, and even better from 0.1 to 20%.

When the pigments or fillers are hydrophilic, they are coated with a film of hydrophobic compound so as to introduce them into the liquid fatty phase of the composition of the invention.

The coating may be a fluorinated coating such as a perfluoroalkyl mono- or diester of phosphoric acid, (acid or salt), a perfluoropolyether, a perfluorocarboxylic or -sulfonic acid, or a perfluoroalkyl phosphate salt of diethanolamine.

The coating may be a coating based on a fluorinated silicone, for example a coating-grafting with a silane having a perfluoroalkyl group.

The coating may also be carried out by means of silicone derivatives, for example a coating-grafting with reactive silicones initially possessing hydrogenosilane groups, a coating-grafting with a diorganosilane such as dimethylchlorosilane or with an alkylalkoxysilane, a coating-grafting with a silane having a glycydoxypropyl group, a coating with a polyglycerolated silicone, or a coating with a silicone-g-polyacrylic or silicone grafted acrylic copolymer.

It is also possible to use a coating with N-acylamino acids, for example N-lauroyllysine, coatings with fatty acids or fatty acid salts of the stearic acid type, coatings with lecithins and coatings with ester oils.

It is also possible to facilitate the dispersion of the hydrophilic particles by means of at least one amphiphilic silicone which plays the role of a surfactant between the hydrophilic particles and the hydrophobic silicone phase.

These amphiphilic silicones contain a silicone part which is compatible with the highly siliconized medium of the compositions of the invention, and a hydrophilic part which may be, for example, the residue of a compound chosen from alcohols and polyols, having from 1 to 12 hydroxyl groups, polyoxyalkylenes containing at least two oxyalkylenated moieties and having from 0 to 20 oxypropylenated moieties and/or from 0 to 20 oxyethylenated moieties. This hydrophilic part therefore has affinity for the hydrophilic particles and promotes their dispersion in the silicone medium.

The amphiphilic silicone may be an oil with no gelling activity. Such oils may consist of:

dimethicone copolyols, optionally containing phenyl groups, alkylmethicone copolyols, polyglycerolated silicones, that is to say silicones with alkylglyceryl ether groups, silicones with perfluorinated side groups and with glycerolated side groups, silicones with polyoxyethylenated/polyoxypropylenated side groups and with perfluorinated side groups, copolymers with a silicone block and with a hydrophilic block other than polyether, for example polyoxazoline or polyethyleneimine, graft copolymers of the silicone-grafted polysaccharide type, copolymers with a silicone block and with a polyoxyethylene/polyoxypropylene block.

The amphiphilic silicone used in the invention may also be an amphiphilic silicone resin which is at least partially crosslinked.

By way of example of such resins, there may be mentioned:

crosslinked silicone resins with alkyl polyether groups, such as polyoxyethylene (POE) and polyoxyethylene/polyoxypropylene (POE/POP), described in U.S. Pat. No. 5,412, 004 [9], and silicone resins partially crosslinked with α,ω-dienes, possessing both hydrophilic POE/POP side chains and hydrophobic alkyl side chains such as those described in EP-A-1 048 686 [10]. The hydrophilic side chains are obtained by reaction with a POE/POP having only one vinyl end, and the alkyl side chains are formed by reaction with an α-olefin having a fatty chain.

In the amphiphilic silicone resin, the silicone part advantageously consists of polydimethylsiloxane.

Gelling Silicone Polymer

The structuring or gelling polymer(s) of the composition are solid at room temperature (25° C.) and atmospheric pressure (760 mmHg) and are soluble in the liquid fatty phase at a temperature of 25 to 250° C.

The expression polymer is understood to mean, for the purpose of the invention, a compound having at least 2 repeating moieties, preferably at least 3 repeating moieties and even better 10 repeating moieties.

In the composition of the invention, the silicone polymer of the gelling system generally represents from 0.5 to 80%, preferably from 2 to 60% and even better from 5 to 40% of the total weight of the composition.

Moreover, the polymer of the gelling system/silicone oil(s) mass ratio is preferably from 0.1 to 50%.

The polymers used as gelling agents in the composition of the invention are polymers of the polyorganosiloxane type such as those described in the documents U.S. Pat. No. 5,874, 069 [3], U.S. Pat. No. 5,919,441 [4], U.S. Pat. No. 6,051,216 [5] and U.S. Pat. No. 5,981,680 [11].

According to the invention, the polymers used as gelling agent may belong to the following two families:

1) polyorganosiloxanes comprising at least two groups capable of establishing hydrogen interactions, these two groups being situated in the polymer chain; and/or 2) polyorganosiloxanes comprising at least two groups capable of establishing hydrogen interactions, these two groups being situated on the grafts or branches.

The polymers to which the invention applies are solids which may be solubilized beforehand in a solvent with hydrogen interactions, capable of breaking the hydrogen interactions of the polymers, such as $C_2$ to $C_8$ lower alcohols and in particular ethanol, n-propanol or isopropanol, before being brought into contact with the silicone oils according to the invention. It is also possible to use these hydrogen interaction "breaking" solvents as cosolvent. These solvents may then be kept in the composition or may be removed by selective evaporation which is well known to persons skilled in the art.

The polymers comprising two groups capable of establishing hydrogen interactions in the polymer chain may be polymers comprising at least one moiety corresponding to the formula:

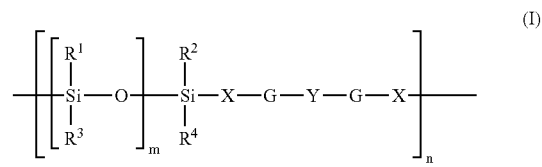

in which:
1) $R^1$, $R^2$, $R^3$ and $R^4$ which may be identical or different, represent a group chosen from:
   linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms,
   $C_6$ to $C_{10}$ aryl groups, optionally substituted with one or more $C_1$ to $C_4$ alkyl groups,
   polyorganosiloxane chains possibly containing one or more oxygen, sulphur and/or nitrogen atoms;
2) the groups X, which may be identical or different, represent a linear or branched $C_1$ to $C_{30}$ alkylenediyl group, possibly containing in its chain one or more oxygen and/or nitrogen atoms;
3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or
4) Y represents a group corresponding to the formula:

in which
T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^5$ represents a linear or branched $C_1$ to $C_{50}$ alkyl group or a polyorganosiloxane chain, possibly comprising one or more ester, amide, urethane, thiocarbamate, urea, thiourea and/or sulphonamide groups, which may possibly be linked to another chain of the polymer;

5) the groups G, which may be identical or different, represent divalent groups chosen from:

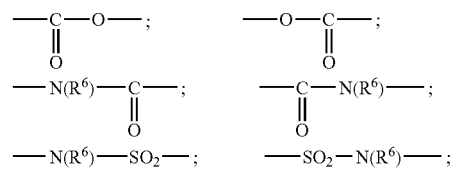

-continued

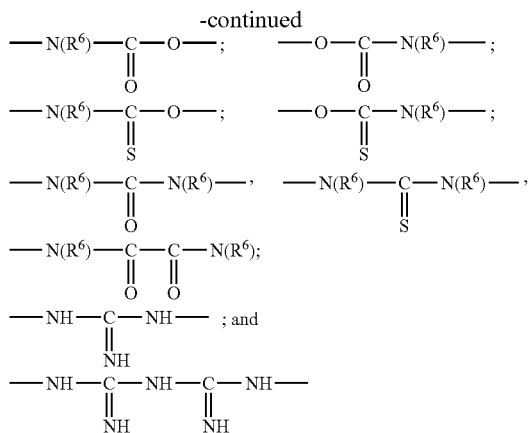

in which $R^6$ represents a hydrogen atom or a linear or branched $C_1$ to $C_{20}$ alkyl group, on condition that at least 50% of the groups $R^6$ of the polymer represent a hydrogen atom and that at least two of the groups G of the polymer are a group other than:

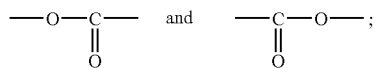

6) n is an integer ranging from 2 to 500 and preferably from 2 to 200, and m is an integer ranging from 1 to 1 000, preferably from 1 to 700 and better still from 6 to 200.

According to the invention, 80% of the groups $R^1$, $R^2$, $R^3$ and $R^4$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) $C_{30}$ to $C_{56}$ branched alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

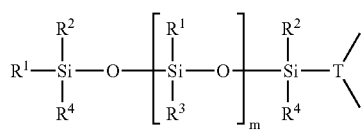

in which $R^1$, $R^2$, $R^3$, $R^4$, T and m are as defined above, and h) polyorganosiloxane chains of formula:

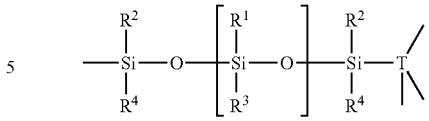

The polyorganosiloxanes of the second family may be polymers comprising at least one moiety corresponding to formula (II):

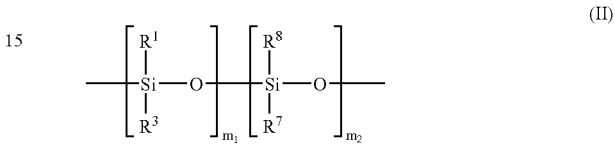

in which $R^1$ and $R^3$, which may be identical or different, are as defined above for formula (I), $R^7$ represents a group as defined above for $R^1$ and $R^3$, or represents the group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents the group of formula —X-G-$R^9$ in which X, G and $R^9$ are as defined above, $m_1$ is an integer ranging from 1 to 998, and $m_2$ is an integer ranging from 2 to 500.

According to the invention, the polymer used as gelling agent may be a homopolymer, that is to say a polymer comprising several identical moieties, in particular moieties of formula (I) or of formula (II).

According to the invention, it is also possible to use a polymer consisting of a copolymer comprising several different moieties of formula (I), that is to say a polymer in which at least one of the groups $R^1$, $R^2$, $R^3$, $R^4$, X, G, Y, m and n is different in one of the moieties. The copolymer may also be formed from several moieties of formula (II), in which at least one of the groups $R^1$, $R^3$, $R^7$, $R^8$, $m_1$ and $m_2$ is different in at least one of the moieties.

It is also possible to use a copolymer comprising at least one moiety of formula (I) and at least one moiety of formula (II), the moieties of formula (I) and the moieties of formula (II) possibly being identical to or different from each other.

According to one variant of the invention, it is also possible to use a copolymer furthermore comprising at least one hydrocarbon-based moiety comprising two groups capable of establishing hydrogen interactions, chosen from ester, amide, sulphonamide, carbamate, thiocarbamate, urea, thiourea, oxamido, guanidino and biguanidino groups, and combinations thereof. These copolymers may be block copolymers or graft copolymers.

According to a first embodiment of the invention, the groups capable of establishing hydrogen interactions are amide groups of formulae —C(O)NH— and —HN—C(O)—.

In this case, the gelling agent may be a polymer comprising at least one moiety of formula (III) or (IV):

(III)

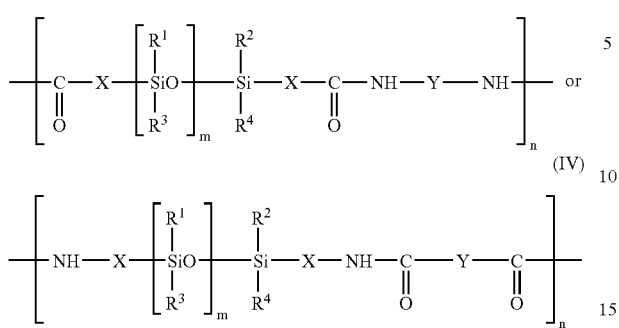

or (IV)

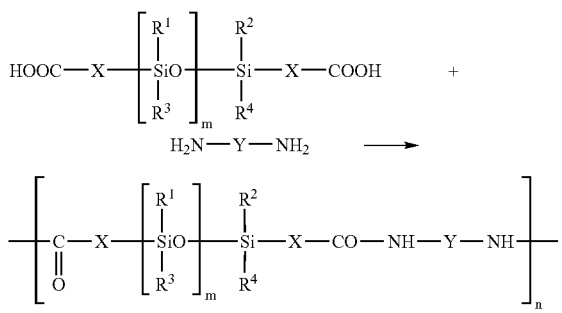

in which $R^1$, $R^2$, $R^3$, $R^4$, X, Y, m and n are as defined above.

Such a moiety may be obtained:

either by a condensation reaction between a silicone containing α,ω-carboxylic acid ends and one or more diamines, according to the following reaction scheme:

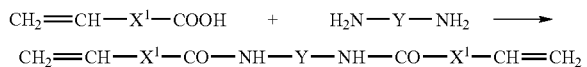

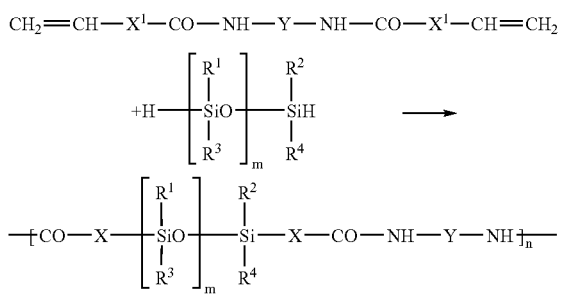

or by reaction of two molecules of α-unsaturated carboxylic acid with a diamine according to the following reaction scheme:

$$CH_2\!=\!CH\!-\!X^1\!-\!COOH + H_2N\!-\!Y\!-\!NH_2 \longrightarrow$$
$$CH_2\!=\!CH\!-\!X^1\!-\!CO\!-\!NH\!-\!Y\!-\!NH\!-\!CO\!-\!X^1\!-\!CH\!=\!CH_2$$

followed by the addition of a siloxane to the ethylenic unsaturations, according to the following scheme:

$$CH_2\!=\!CH\!-\!X^1\!-\!CO\!-\!NH\!-\!Y\!-\!NH\!-\!CO\!-\!X^1\!-\!CH\!=\!CH_2$$

[siloxane structure]

in which $X^1$—$(CH_2)_2$— corresponds to X defined above and Y, $R^1$, $R^2$, $R^3$, $R^4$ and m are as defined above;

or by reaction of a silicone containing α,ω-$NH_2$ ends and a diacid of formula HOOC—Y—COOH according to the following reaction scheme:

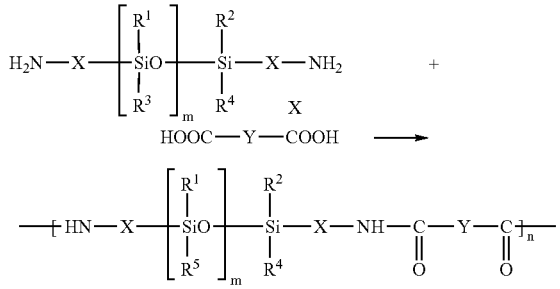

In these polyamides of formula (III) or (IV), m is preferably in the range from 1 to 700, more preferably from 15 to 500 and better still from 15 to 45, and n is in particular in the range from 1 to 500, preferably from 1 to 100 and better still from 4 to 25, X is preferably a linear or branched alkylene chain containing from 1 to 30 carbon atoms and in particular 3 to 10 carbon atoms, and Y is preferably an alkylene chain that is linear or branched or that possibly comprises rings and/or unsaturations, containing from 1 to 40 carbon atoms, in particular from 1 to 20 carbon atoms and better still from 2 to 6 carbon atoms, in particular 6 carbon atoms.

In formulae (III) and (IV), the alkylene group representing X or Y can optionally contain in its alkylene portion at least one of the following elements:

1) 1 to 5 amide, urea or carbamate groups,
2) a $C_5$ or $C_6$ cycloalkyl group, and
3) a phenylene group optionally substituted with 1 to 3 identical or different $C_1$ to $C_3$ alkyl groups.

In formulae (III) and (IV), the alkylene groups may also be substituted with at least one element chosen from the group consisting of:

a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

In these formulae (III) and (IV), Y may also represent:

in which $R^5$ represents a polyorganosiloxane chain and T represents a group of formula:

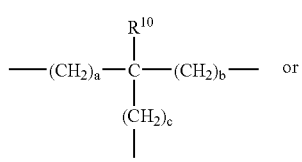

or

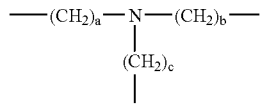

in which a, b and c are, independently, integers ranging from 1 to 10, and $R^{10}$ is a hydrogen atom or a group such as those defined for $R^1$, $R^2$, $R^3$ and $R^4$.

In formulae (III) and (IV), $R^1$, $R^2$, $R^3$ and $R^4$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different moieties of formula (III) or (IV).

Thus, the polymer may be a polyamide containing several moieties of formula (III) or (IV) of different lengths, i.e. a polyamide corresponding to the formula:

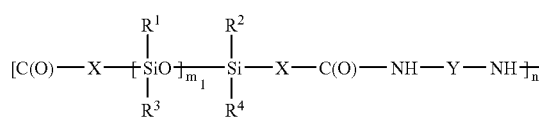

in which X, Y, n and $R^1$ to $R^4$ have the meanings given above, $m_1$ and $m_2$, which are different, are chosen in the range from 1 to 1 000, and p is an integer ranging from 2 to 300.

In this formula, the moieties may be structured to form either a block copolymer, or a random copolymer or an alternating copolymer. In this copolymer, the moieties may be not only of different lengths, but also of different chemical structures, for example containing different groups Y. In this case, the copolymer may correspond to the formula:

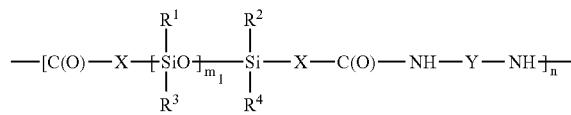

in which $R^1$ to $R^4$, X, Y, $m_1$, $m_2$, n and p have the meanings given above and $Y^1$ is different from Y but chosen from the groups defined for Y. As previously, the various moieties may be structured to form either a block copolymer, or a random copolymer or an alternating copolymer.

In this first embodiment of the invention, the gelling agent may also consist of a graft copolymer. Thus, the polyamide containing silicone units may be grafted and optionally crosslinked with silicone chains containing amide groups. Such polymers may be synthesized with trifunctional amines.

In this case, the copolymer may comprise at least one moiety of formula:

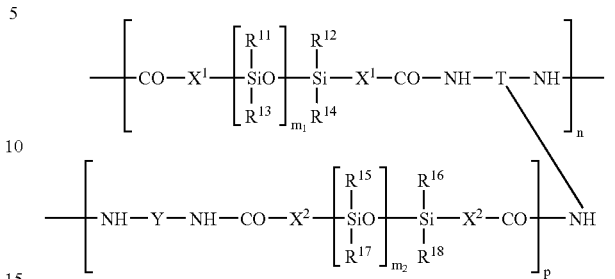

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1000, and p is an integer ranging from 2 to 500.

In formula (VII), it is preferred that:

p is in the range from 1 to 25 and better still from 1 to 7, $R^{11}$ to $R^{18}$ are methyl groups, T corresponds to one of the following formulae:

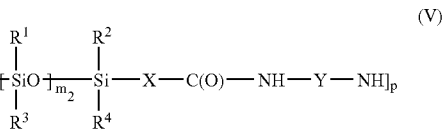

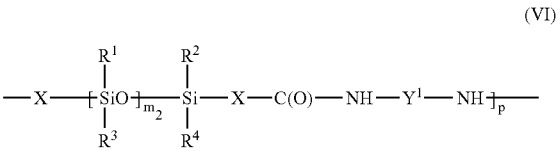

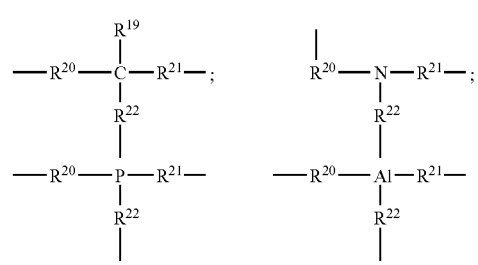

in which $R^{19}$ is a hydrogen atom or a group chosen from the groups defined for $R^1$ to $R^4$, and $R^{20}$, $R^{21}$ and $R^{22}$ are, independently, linear or branched alkylene groups, and more preferably corresponds to the formula:

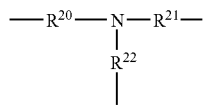

in particular with $R^{20}$, $R^{21}$ and $R^{22}$ representing —$CH_2$—$CH_2$—, $m_1$ and $m_2$ are in the range from 15 to 500 and better still from 15 to 45, $X^1$ and $X^2$ represent —$(CH_2)_{10}$—, and Y represents —$CH_2$—.

These polyamides containing a grafted silicone moiety of formula (VII) may be copolymerized with polyamide-silicones of formula (II) to form block copolymers, alternating copolymers or random copolymers. The weight percentage of grafted silicone moieties (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to the invention, the preferred siloxane-based polyamides are:

polyamides of formula (III) in which m is from 15 to 50;

mixtures of two or more polyamides in which at least one polyamide has a value of m in the range from 15 to 50 and at least one polyamide has a value of m in the range from 30 to 50;

polymers of formula (V) with $m_1$ chosen in the range from 15 to 50 and $m_2$ chosen in the range from 30 to 500 with the portion corresponding to $m_1$ representing 1% to 99% by weight of the total weight of the polyamide and the portion corresponding to $m_2$ representing 1% to 99% by weight of the total weight of the polyamide;

mixtures of polyamide of formula (III) combining 1) 80% to 99% by weight of a polyamide in which n is equal to 2 to 10 and in particular 3 to 6, and 2) 1% to 20% of a polyamide in which n is in the range from 5 to 500 and in particular from 6 to 100;

polyamides corresponding to formula (VI) in which at least one of the groups Y and $Y^1$ contains at least one hydroxyl substituent;

polyamides of formula (III) synthesized with at least one portion of an activated diacid (diacid chloride, dianhydride or diester) instead of the diacid;

polyamides of formula (III) in which X represents —$(CH_2)_3$— or —$(CH_2)_{10}$—; and polyamides of formula (III) in which the polyamides end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

According to the invention, the ends of the polymer chains may end with:

a $C_1$ to $C_{50}$ alkyl ester group by introducing a $C_1$ to $C_{50}$ monoalcohol during the synthesis, a $C_1$ to $C_{50}$ alkylamide group by taking as stopping group a monoacid if the silicone is α,ω-diaminated, or a monoamine if the silicone is an α,ω-dicarboxylic acid.

According to one embodiment variant of the invention, it is possible to use a copolymer of silicone polyamide and of hydrocarbon-based polyamide, i.e. a copolymer comprising moieties of formula (III) or (IV) and hydrocarbon-based polyamide moieties. In this case, the polyamide-silicone moieties may be arranged at the ends of the hydrocarbon-based polyamide.

Polyamide-based gelling agents containing silicones may be produced by silylic amidation of polyamides based on fatty acid dimer. This approach involves the reaction of free acid sites existing on a polyamide as end sites, with oligosiloxane-monoamines and/or oligosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and better still 2, 6, 9.5, 12, 13.5, 23 or 31 siloxane groups, may be used for the reaction with hydrocarbon-based polyamides based on fatty acid dimers. Siloxane diamines containing 13.5 siloxane groups are preferred, and the best results are obtained with the siloxane diamine containing 13.5 siloxane groups and polyamides containing high numbers of carboxylic acid end groups.

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide containing free amine groups, by amidation reaction with a siloxane containing an acid group.

It is also possible to prepare a gelling agent based on a copolymer between a hydrocarbon-based polyamide and a silicone polyamide, by transamidation of a polyamide having, for example, an ethylenediamine constituent, with an oligosiloxane-α,ω-diamine, at high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a graft copolymer comprising a hydrocarbon-based polyamide backbone with pendent oligosiloxane groups.

This may be obtained, for example:

by hydrosilylation of unsaturated bonds in polyamides based on fatty acid dimers;

by silylation of the amide groups of a polyamide; or by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

According to a second embodiment of the invention, the gelling agent consists of a homopolymer or a copolymer comprising urethane or urea groups.

As previously, the polymer may comprise polyorganosiloxane moieties containing two or more urethane and/or urea groups, either in the backbone of the polymer or on side chains or as pendent groups.

The polymers comprising at least two urethane and/or urea groups in the backbone may be polymers comprising at least one moiety corresponding to the following formula:

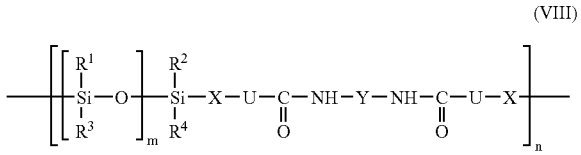
(VIII)

in which $R^1$, $R^2$, $R^3$, $R^4$, X, Y, m and n have the meanings given above for formula (I), and U represents —O— or —NH—, such that:

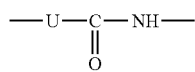

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —$(CH_2)_6$— group is used.

Y may also represent a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to the formula:

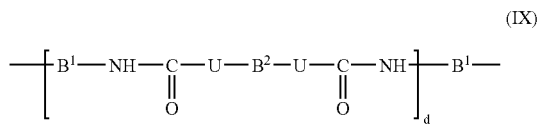
(IX)

in which $B^1$ is a group chosen from the groups given above for Y, U is —O— or —NH— and $B^2$ is chosen from:

linear or branched $C_1$ to $C_{40}$ alkylene groups, which can optionally bear an ionizable group such as a carboxylic acid or sulphonic acid group, or a neutralizable or quaternizable tertiary amine group, $C_5$ to $C_{12}$ cycloalkylene groups, optionally bearing alkyl substituents, for example one to three methyl or ethyl groups, or alkylene substituents, for example the diol radical: cyclohexanedimethanol, phenylene groups that may optionally bear $C_1$ to $C_3$ alkyl substituents, and groups of formula:

in which T is a hydrocarbon-based trivalent radical possibly containing one or more heteroatoms such as oxygen, sulphur and nitrogen and $R^5$ is a polyorganosiloxane chain or a linear or branched $C_1$ to $C_{50}$ alkyl chain.

T can represent, for example:

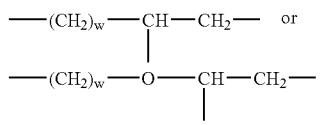

with w being an integer ranging from 1 to 10 and $R^5$ being a polyorganosiloxane chain.

When Y is a linear or branched $C_1$ to $C_{40}$ alkylene group, the —$(CH_2)_2$— and —$(CH_2)_6$— groups are preferred.

In the formula given above for Y, d may be an integer ranging from 0 to 5, preferably from 0 to 3 and more preferably equal to 1 or 2.

Preferably, $B^2$ is a linear or branched $C_1$ to $C_{40}$ alkylene group, in particular —$(CH_2)_2$— or —$(CH_2)_6$— or the group:

with $R^5$ being a polyorganosiloxane chain.

As previously, the polymer constituting the gelling agent may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

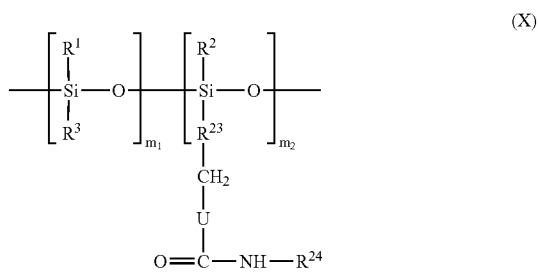
(X)

in which $R^1$, $R^2$, $R^3$, $m_1$ and $m_2$ have the meanings given above for formula (I), U represents O or NH, $R^{23}$ represents a $C_1$ to $C_{40}$ alkylene group, optionally comprising one or more heteroatoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one moiety of formula (X) contain siloxane units and urea or urethane groups, and they may be used as gelling agents in the compositions of the invention.

The siloxane polymers may have a single urea or urethane group per branch or may have branches containing two urea or urethane groups, or alternatively they may contain a mixture of branches containing one urea or urethane group and branches containing two urea or urethane groups.

They may be obtained from branched polysiloxanes, comprising one or two amino groups per branch, by reacting these polysiloxanes with monoisocyanates.

As examples of starting polymers of this type containing amino and diamino branches, mention may be made of the polymers corresponding to the following formulae:

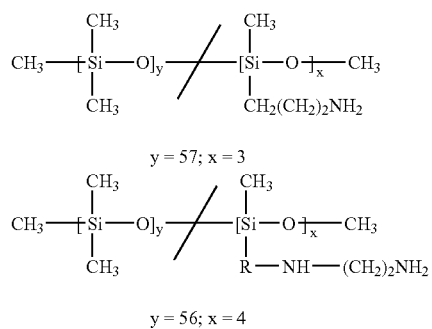

y = 57; x = 3 y = 56; x = 4

In these formulae, the symbol "/" indicates that the segments may be of different lengths and in a random order, and R represents a linear aliphatic group preferably containing 1 to 6 carbon atoms and better still 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form the groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane moieties and groups capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

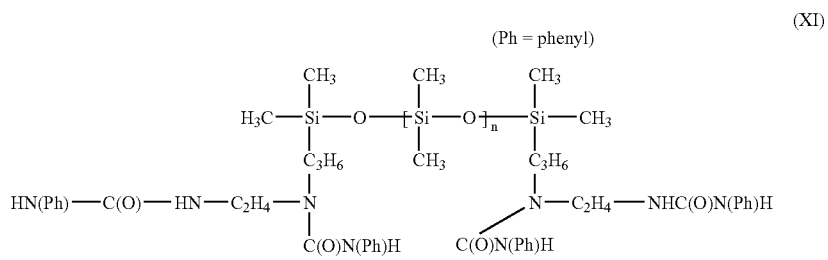

(XI)

in which Ph is a phenyl group and n is a number from 0 to 300, in particular from 0 to 100, for example 50.

This polymer is obtained by reacting the following polysiloxane containing amino groups:

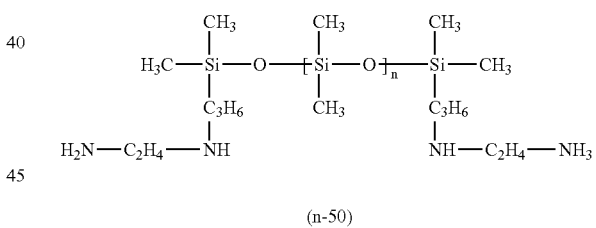

(n-50)

with phenyl isocyanate.

The polymers of formula (VIII) comprising urea or urethane groups in the chain of the silicone polymer may be obtained by reaction between a silicone containing α,ω-NH$_2$ or —OH end groups, of formula:

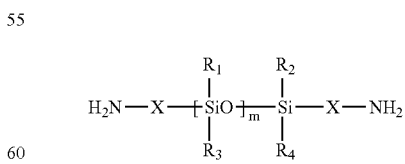

in which m, $R^1$, $R^2$, $R^3$, $R^4$ and X are as defined for formula (I), and a diisocyanate OCN—Y—NCO in which Y has the meaning given in formula (I); and optionally a diol or diamine coupling agent of formula H$_2$N—B$^2$—NH$_2$ or HO—B$^2$—OH, in which B$^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (II) or (III), it is possible to use in the invention polyurethane or polyurea silicones containing moieties of different length and structure, in particular moieties whose lengths differ by the number of silicone moieties. In this case, the copolymer may correspond, for example, to the formula:

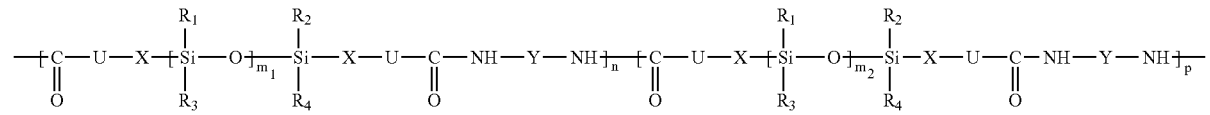

(XII)

in which $R^1$, $R^2$, $R^3$, $R^4$, X, Y and U are as defined for formula (VIII) and $m_1$, $m_2$, n and p are as defined for formula (V).

Branched polyurethane or polyurea silicones may also be obtained using, instead of the diisocyanate OCN—Y—NCO, a triisocyanate of formula:

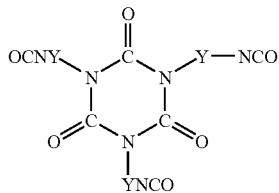

A polyurethane or polyurea silicone containing branches comprising an organosiloxane chain with groups capable of establishing hydrogen interactions is thus obtained. Such a polymer comprises, for example, a moiety corresponding to the formula:

polymers of formula (VIII) in which m is from 15 to 50;

mixtures of two or more polymers in which at least one polymer has a value of m in the range from 15 to 50 and at least one polymer has a value of m in the range from 30 to 50;

polymers of formula (XII) with $m_1$ chosen in the range from 15 to 50 and $m_2$ chosen in the range from 30 to 500 with the portion corresponding to $m_1$ representing 1% to 99% by weight of the total weight of the polymer and the portion corresponding to $m_2$ representing 1% to 99% by weight of the total weight of the polymer;

mixtures of polymer of formula (VIII) combining 1) 80% to 99% by weight of a polymer in which n is equal to 2 to 10 and in particular 3 to 6, and 2) 1% to 20% of a polymer in which n is in the range from 5 to 500 and in particular from 6 to 100, copolymers comprising two moieties of formula (VIII) in which at least one of the groups Y contains at least one hydroxyl substituent;

polymers of formula (VIII) synthesized with at least one portion of an activated diacid (diacid chloride, dianhydride or diester) instead of the diacid;

polymers of formula (VIII) in which X represents —$(CH_2)_3$— or —$(CH_2)_{10}$—; and polymers of formula (VIII) in which the polymers end with a monofunctional chain chosen from the group consisting of monofunctional amines, monofunctional acids, monofunc-

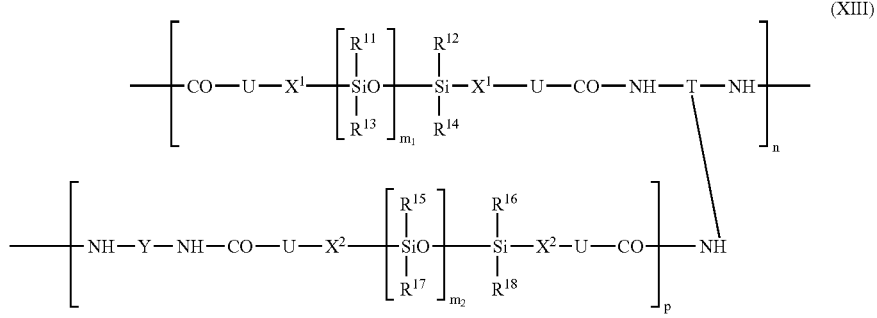

(XIII)

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1 000, and p is an integer ranging from 2 to 500.

As in the case of the polyamides, this copolymer can also comprise polyurethane silicone moieties without branching.

In this second embodiment of the invention, the siloxane-based polyureas and polyurethanes that are preferred are:

tional alcohols, including fatty acids, fatty alcohols and fatty amines, such as, for example, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an α,ω-difunctional block of non-silicone nature, for example a polyester, a polyether or a polyolefin.

As has been seen previously, gelling agents consisting of homopolymers or copolymers of the invention may contain siloxane moieties in the main chain of the polymer and groups capable of establishing hydrogen interactions, either in the main chain of the polymer or at the ends thereof, or on side chains or branches of the main chain. This may correspond to the following five arrangements:

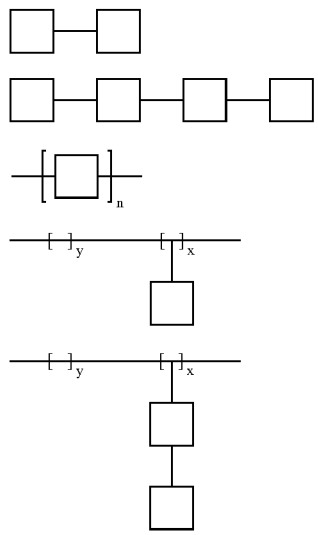

in which the continuous line is the main chain of the siloxane polymer and the squares represent the groups capable of establishing hydrogen interactions.

In case (1), the groups capable of establishing hydrogen interactions are arranged at the ends of the main chain. In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. The values n, x and y are such that the polymer has the desired properties in terms of an agent for gelling fatty phases based on silicone oil.

According to the invention, the structuring of the liquid fatty phase containing at least one silicone oil, is obtained with the aid of one or more of the polymers mentioned above, in combination with one or more non-polymeric organogelling agents.

As examples of polymers that may be used, mention may be made of the silicone polyamides obtained in accordance with Examples 1 and 2 of document U.S. Pat. No. 5,981,680.

The polymers and copolymers used in the gelling system of the composition of the invention advantageously have a softening point from 40 to 190° C. Preferably, they have a softening point ranging from 50 to 140° C. and better still from 70° C. to 120° C. This softening point is lower than that of the known structuring polymers, which facilitates the use of the polymers that are the subject of the invention, allows the use of volatile oils and limits the deteriorations of the liquid fatty phase.

They have good solubility in silicone oils and produce macroscopically homogeneous compositions. Preferably, they have an average molecular mass from 500 to 200 000, for example from 80 000 to 200 000, preferably from 2 000 to 30 000.

Non-Polymeric Organogelling Agent

The composition according to the invention contains one or more organogelling agents. This or these organogelling agent(s) make it possible to reinforce the mechanical properties of the composition, in particular the properties of resistance to shearing when it is in the form of a stick. This reinforcement results in a stick which is resistant to the shearing produced during the application of the composition to the lips or the skin, but also to the superficial body growths. Thus, it is possible to manufacture a lipstick having a stick diameter of 12.7 mm, which diameter corresponds to that customarily used in conventional lipsticks.

According to the invention, the composition comprises at least one organogelling agent. An organogelling agent is defined here as comprising a non-polymeric organic compound whose molecules may be capable of establishing, with each other, at least one physical interaction leading to self-aggregation of the molecules with formation of a three-dimensional macromolecular network which may be responsible for the gelling of the liquid fatty phase. The network can result from the formation of a network of fibrils (due to the stacking or aggregation of the organic gelling molecules), immobilizing the molecules of the liquid fatty phase. Depending on the nature of the organogelling agent, the interconnected fibrils have variable sizes which may range from a few nanometres to 1 μm or even several micrometres. These fibrils can occasionally combine to form ribbons or columns.

The term "gelling" means a thickening of the medium which may lead to a gelatinous consistency and even to a rigid, solid consistency which does not run under its own weight. The capacity to form this network of fibrils, and thus the gelling, depends on the nature (or the chemical category) of the organogelling agent, the nature of the substituents carried by its molecules for a given chemical category, and the nature of the liquid fatty phase. For example, this gelling is reversible under the action of an external stimulus such as temperature.

The physical interactions are diverse but may exclude cocrystallization. These physical interactions are for example interactions chosen from self-complementary hydrogen interactions, π interactions between unsaturated nuclei, dipolar interactions, and coordination bonds with organometallic derivatives. The establishment of these interactions can often be promoted by the architecture of the molecule, for example by nuclei, unsaturations, and the presence of asymmetric carbon. In general, each molecule of an organogelling agent can establish several types of physical interaction with a neighbouring molecule. Thus, in one embodiment, the molecules of the organogelling agent according to the invention may comprise at least one group capable of establishing a hydrogen bond, for example at least two groups capable of establishing a hydrogen bond; at least one aromatic nucleus, for example at least two aromatic nuclei; at least one bond with ethylenic unsaturation; and/or at least one asymmetric carbon. The groups capable of forming a hydrogen bond may be chosen, for example, from the hydroxyl, carbonyl, amine, carboxylic acid, amide, benzyl, sulphonamide, carbamate, thiocarbamate, urea, thiourea, oxamido, guanidino and biguanidino groups.

The organogelling agents of the invention may be soluble in the liquid fatty phase at room temperature and at atmospheric pressure. They may be solid or liquid at room temperature and at atmospheric pressure.

Organogelling agents which may be used in the invention are, for example, those described in the document "Specialist Surfactants" published by D. Robb, 1997, pp. 209-263, chapter 8, by P. Terech [12], and the documents FR-A-2 796 276 [13] and FR-A-2 811 552 [14]. The organogelling agents described in these documents are, for example, chosen from:

hydroxylated fatty carboxylic acids having a linear or branched, aliphatic carbon chain containing, in one embodiment, at least 8 carbon atoms such as at least 12 carbon atoms, for example 12-hydroxystearic acid and 12-hydroxyoleic acid, and their salts such as the alkali metal salts (in particular the Li, Na and K salts) and the alkaline-earth metal salts (for example the magnesium salts) or esters thereof resulting from esterification with a monoalcohol or a polyol having a saturated or unsaturated, linear or cyclic chain of 1 to 6 carbon atoms;

amides of carboxylic acids such as tricarboxylic acids, for example cyclohexanetricarboxamides (see [13]), these amides corresponding, for example, to the formula (XV) given below;

amides or esters of amino acids, for example esters of alanine and amides of valine (such as those described in the book "Specialist Surfactants") [12];

amides of N-acylamino acids, for example the diamides resulting from the action of an N-acylamino acid with amines containing from 1 to 22 carbon atoms, such as those described in WO-93/23008 [15], for example N-acylglutamides in which the acyl group is a $C_8$ to $C_{22}$ alkyl chain, and the dibutylamide of N-laurylglutamic acid, such as the product sold or manufactured by the company AJINOMOTO under the name GP-1;

diamides having hydrocarbon chains each containing from 1 to 22 carbon atoms, for example from 6 to 18 carbon atoms, these hydrocarbon chains being optionally substituted with ester, urea or fluoro groups (see [14]), these diamides being for example those of formula (XIV) given below; and such as those resulting from the reaction of diaminocyclohexane, for example trans-diaminocyclohexane, and of an acid chloride;

amides or amines of steroids, such as those of deoxycholic, cholic, apocholic or lithocholic acids, and salts thereof, for example D-17,17-dipropyl-17a-aza-5α-homoandrostan-3β-ol or D-17, 17-dipropyl-17a-aza-5α-homoandrostan-3β-ol 17a-oxy;

compounds containing several aromatic nuclei (2 or 3), such as the anthrylic derivatives comprising at least two alkyl chains containing from 8 to 30 carbon atoms, for example 2,3-bis(n-decyloxy)anthracene or 2,3-bis(n-decyloxy)anthraquinone, or comprising a steroid group, for example cholesteryl 4-(2-anthryloxy)butanoate or cholesteryl anthraquinone-2-carboxylate and derivatives thereof;

azobenzene steroids such as those described in the book "Specialist Surfactants" [12];

organometallic compounds, for example mononuclear copper β-diketonate (the octasubstituted copper complex of bis(3,4-nonyloxybenzoyl)methane), binuclear copper tetracarboxylates or Zn (II) complexes of trisubstituted (para-carboxyphenyl)porphyrine;

surfactants in salt form comprising at least two linear or branched alkyl chains, such as alkali metal or aluminium alkyl phosphates comprising two alkyl chains containing from 8 to 30 carbon atoms, for example the aluminium salt of hexadecyl phosphate ($C_{16}DP$—Al) or bis(2-ethylhexyl)phosphate and alkali metal (Na) salts thereof, bis(2-ethylhexyl)sulphosuccinate and alkali metal (Na) salts thereof;

benzylidene sorbitols or alditols and derivatives thereof, for example 1,3:2,4-di-o-benzylidene-D-sorbitol;

cyclodipeptides which are cyclic condensates of two amino acids such as those described in the book "Specialist Surfactants" [12];

cyclic compounds or alkylene compounds comprising two urea or urethane groups such as dialkylurea cyclohexane, having for example the formula (XVI) given below;

alkylaryl derivatives of cyclohexanol in which the alkyl chain is linear or branched and comprises from 1 to 22 carbon atoms, and the aryl part is for example a phenyl group, these derivatives being for example 4-tert-butyl-1-phenylcyclohexanol;

calixarenes such as those mentioned in the book "Specialist Surfactants" [12];

combinations of 2,4,6-triaminopyrimidines which are substituted with an alkyl chain and of dialkylbarbituric acid, the alkyl chains thereof being linear or branched and comprising from 1 to 22 carbon atoms;

the organogelling agents defined in the document WO-A-01/07007 [16] corresponding to the general formula (XVII):

$$Q\text{-}O\text{---}W\text{---}(CHOH)_s\text{---}W^1\text{---}O\text{-}Q^1 \quad (XVII)$$

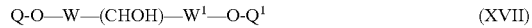

in which W and $W^1$, which may be identical or different, are chosen from —$CH_2$— and —CO—, and in which Q and $Q^1$, which may be identical or different, are a hydrocarbon chain chosen from saturated or unsaturated, linear or branched hydrocarbon chains containing at least 6 carbon atoms, and in which s is an integer from 2 to 4; such as the compounds in which W=$W^1$50 —$CH_2$— and s=2 and the compounds in which W=$W^1$=—CO— and s=4;

gluconamide derivatives such as those described in the article R. J. H. Hafkamp, Chem. Commun., (1997), pages 545-46 [17], and in the article J. Org. Chem., vol. 64, No. 2; 412-26 (1999) [18], corresponding to the formula (XVIII):

$$R^{25}\text{---}NH\text{---}CO\text{---}[CH(OH)]_4\text{---}CH_2R^{26} \quad (XVIII)$$

in which $R^{25}$ is a hydrocarbon chain chosen from saturated or unsaturated, linear, branched and cyclic hydrocarbon chains having from 1 to 30 carbon atoms, for example octyl, it being possible for this hydrocarbon chain to optionally comprise at least one heteroatom such as N, O and S, and in which $R^{26}$ represents —O—CO—$R^{27}$ or —O—$R^{27}$ with $R^{27}$ being chosen from linear and branched alkyl chains containing from 1 to 20 carbon atoms, $C_5$-$C_8$ cycloaliphatic chains and aromatic chains, $C_5$-$C_8$ heterocycles comprising N, O or S atoms, and for example the compounds in which $R^{26}$ is a saturated or unsaturated $C_5$-$C_8$ heterocycle comprising an N, O or S atom such that $R^{26}$ represents the imidazolyl group, cyclic ether derivatives of the compounds of formula (XVIII) having the formula (XIX):

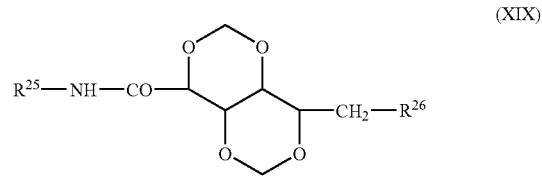

in which $R^{25}$ and $R^{26}$ have the same meaning as in formula (XVIII);

provided that $R^{25}$ and $R^{26}$ are such that they allow the gelling of the liquid fatty phase;

diamide, diurea or diurethane derivatives of amino acids such as:

a) the bisoxalylamides of amino acids cited in the article by M. Jokic, J. Chem. Soc., Chem. Commun., pages 1723-24 (1995) [19], of formula:

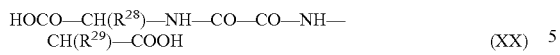
    HOCO—CH($R^{28}$)—NH—CO—CO—NH—CH($R^{29}$)—COOH    (XX)

in which $R^{28}$ and $R^{29}$, which may be identical or different, are a characteristic group of the amino acid, chosen for example from:

—$CH_2$—CH($CH_3$)$_2$; —$C_6H_5$; —$CH_2$—$C_6H_5$; —CH($CH_3$)$_2$;

b) the amide and urea derivatives of a lysine ester such as those mentioned in the article by K. Hanabusa, Chemistry Letters, pp. 1070-71, 2000 [20], such as the ethyl or methyl ester of N$^\epsilon$-lauroyl-N$^\alpha$-stearylaminocarbonyl-L-lysine and derivatives having the formula:

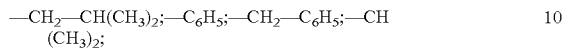
    $C_{11}$—$H_{23}$—CO—NH—($CH_2$)$_4$—CH(COO$R^{30}$)—NH—CO—$R^{31}$ in which $R^{30}$=—$CH_3$ or —$C_2H_5$ and $R^{31}$=—NH—($CH_2$)$_{17}$—$CH_3$ or —NH—($CH_2$)$_n$—$CH_3$ with n=1 to 30.

c) diamide derivatives of benzenedicarboxylic acids and of valine such as those mentioned in the article by K. Hanabusa, Chemistry Letters, pp. 767-8, 1999 [21], corresponding for example to the formulae:

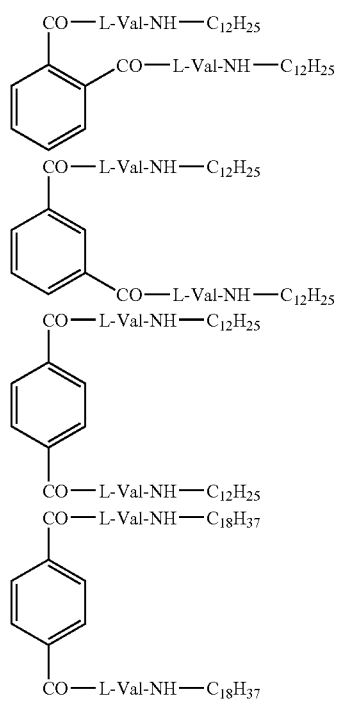

in which -L-Val- represents:

—NH—CH[CH($CH_3$)$_2$)]—CO—;

monoalkyloxamides such as those described by X. Luo, Chem. Commun., pp. 2091-92, 2000 [22], for example of formula:

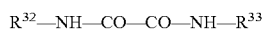
    $R^{32}$—NH—CO—CO—NH—$R^{33}$ in which $R^{32}$ and $R^{33}$, which may be identical or different, are a hydrocarbon chain chosen from saturated or unsaturated, linear, branched and cyclic hydrocarbon chains having from 1 to 30 carbon atoms; and which may contain one or more heteroatoms such as O, N and S;

bolaamphiphiles with a 1-glucosamide head such as N,N'-bis(β-D-glucopyranosyl)-n-alkane-1-dicarboxamide, such as the compounds mentioned in the article by T. Shimizu, J. Am. Chem. Soc., 119, pp. 2812-18, 1997 [23], corresponding to the formula (XXI):

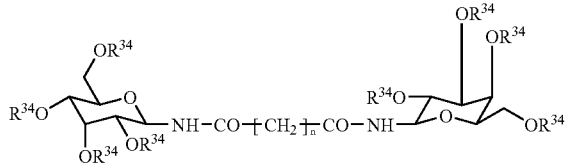

in which n is an integer from 2 to 30, $R^{34}$ is —H or —CO—$R^{35}$ in which $R^{35}$ is a $C_1$-$C_{20}$ alkyl group, for example the compound in which $R^{34}$ represents —CO—$CH_3$;

bolaamphiphilic amides derived from amido acids mentioned by K. Hanabusa, Adv. Mater., 9, No. 14, 1997, pp. 1095-1097 [24], corresponding to the formulae:

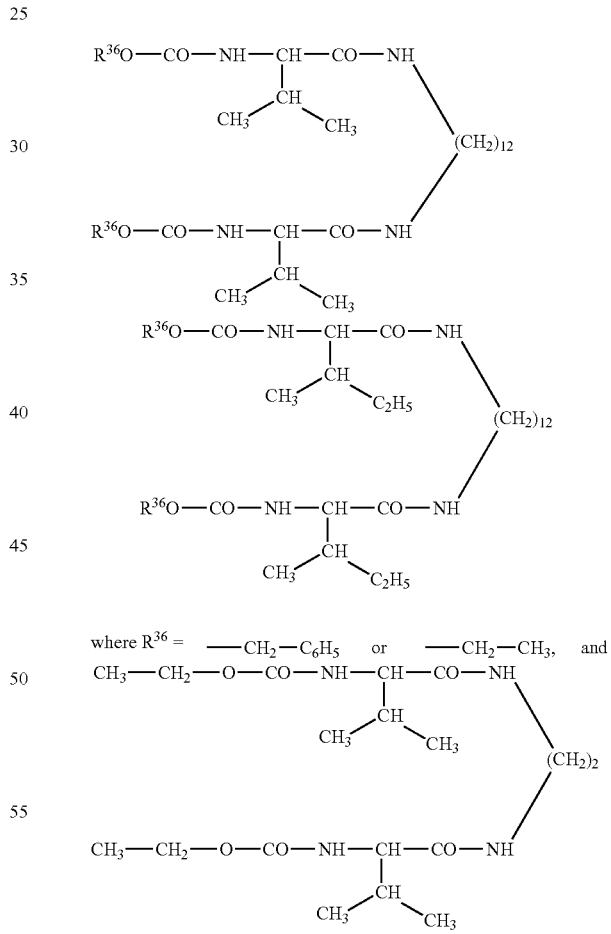

2-alkyl-2-ammoniumisobutyl acetate p-toluenesulphonate salts such as those described by K. Hanabusa, Colloïd Polym. Sci., 276, pp. 252-59, 1998 [25], corresponding to the formula (XXII):

    $p$-$CH_3$—$C_6H_4$—$SO_3^-$ $^+H_3N$—CH($R^{37}$)—CO—O$R^{38}$    (XXII)

in which $R^{37}$ represents:

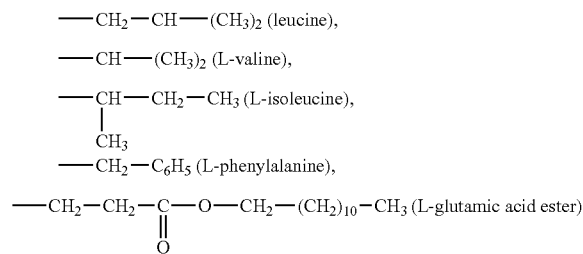

$R^{38}$ represents:

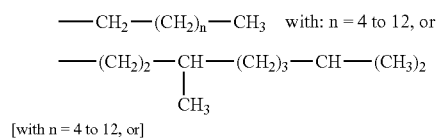

[with n = 4 to 12, or]

fatty esters of cellobiose such as those mentioned in WO-A-00/61080 [26] and WO-A-00/61081 [27] of formula (XXIII):

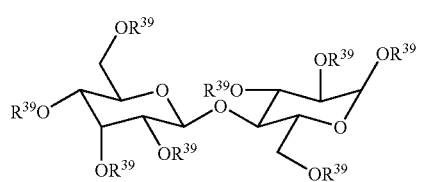

in which $R^{39}$=—CO—$R^{40}$ and $R^{40}$ represents an alkyl or alkylene group of 5 to 12 carbon atoms;

the organogelling agents having two urea groups and two carbamate groups mentioned in U.S. Pat. No. 6,156,325 [28] of formula (XXIV):

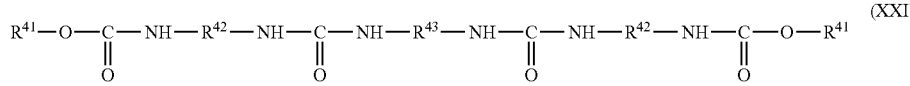

in which $R^{41}$ is an alkyl group of 4 to 42 carbon atoms optionally containing oxygen atoms, and $R^{42}$ and $R^{43}$, which may be identical or different, represent $C_2$ to $C_{20}$ alkylene, $C_5$ to $C_{10}$ cycloalkylene or $C_5$ to $C_{10}$ cycloarylene groups; diamides of formula (XXV) or (XXVI):

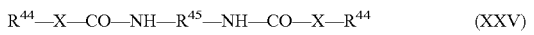

or

in which the groups $R^{44}$, which may be identical or different, represent a saturated or unsaturated, linear or branched $C_8$-$C_{60}$ hydrocarbon chain, the group(s) $R^{44}$ optionally comprising a hydroxyl group or at least one heteroatom such as N, O, S or Si, $R^{45}$ is a hydrocarbon-based group chosen from linear, branched and cyclic $C_1$ to $C_{50}$ groups and $C_5$ to $C_8$ arylene groups optionally substituted with one or more $C_1$-$C_4$ alkyl groups, and X represents —O— or —NH—.

It is also possible to use mixtures of the various organogelling agents described above.

According to one embodiment, the organogelling agent is chosen from amides of amino acids such as N-acylamino acids and cyclohexanetricarboxamides, and mixtures thereof.

Organogelling Agents of Formula (XIV)

According to the invention, the organogelling agent may be a compound of formula (XIV) below:

$$R^{46}—CO—NH-A-NH—CO—R^{47} \quad (XIV)$$

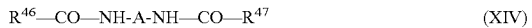

in which $R^{46}$ and $R^{47}$, which may be identical or different, represent a hydrogen atom or a hydrocarbon chain chosen from saturated and unsaturated, linear, branched and cyclic hydrocarbon chains containing from 1 to 22 carbon atoms, for example from 6 to 18 carbon atoms, in particular 10 to 14 carbon atoms, optionally substituted with at least one group chosen from aryl (—$C_6H_5$), ester (—COOR$^{48}$ with $R^{48}$ being an alkyl group of 2 to 12 carbon atoms), amide (—CONHR$^{48}$ with $R^{48}$ as defined above), urethane (—OCONHR$^{48}$ with $R^{48}$ as defined above), and urea (—NHCONHR$^{48}$ with $R^{48}$ as defined above) groups; and/or optionally containing from 1 to 3 heteroatoms chosen from O, S and N; and/or optionally substituted with 1 to 4 halogen atoms, in particular fluorine atoms, and/or 1 to 3 hydroxyl radicals, provided that $R^{46}$ and $R^{47}$ are not both a hydrogen atom, and A is chosen from saturated and unsaturated, linear, cyclic and branched hydrocarbon chains containing from 1 to 18 carbon atoms, for example from 2 to 12 carbon atoms, in particular from 4 to 12 carbon atoms, optionally substituted with at least one group chosen from aryl (—$C_6H_5$), ester (—COOR$^{48}$), amide (—CONHR$^{48}$), urethane (—OCONHR$^{48}$) and urea (—NHCONHR$^{48}$) groups; and/or optionally containing from 1 to 3 heteroatoms chosen from O, S and N; and/or optionally substituted with 1 to 4 halogen atoms, such as fluorine atoms, and/or 1 to 3 hydroxyl radicals.

In formula (XIV), the expression "unsaturated hydrocarbon chain" means a chain which comprises at least one C=C double bond or at least one C≡C triple bond, it being possible for the chain to be also optionally substituted with at least one group chosen from aryl, ester, amide, urethane and urea groups; and/or to optionally comprise at least one heteroatom chosen from O, S and N; and/or to be optionally substituted with at least one fluorine atom and/or one hydroxyl radical.

The expression "hydrocarbon chain comprising an oxygen, sulphur or nitrogen atom" in formula (XIV) includes in particular a hydrocarbon chain comprising a carbonyl (C=O), amine (—$NH_2$ or —NH—), thiol (—SH), thioether or ether group.

The compounds correspond, for example, to formula (XIV) in which:

1) —A is chosen from saturated and unsaturated, but non-aromatic, optionally branched hydrocarbon nuclei containing from 4 to 12 carbon atoms, for example from 5 to 7 carbon atoms, optionally substituted with the substituents mentioned above and/or optionally comprising at least one heteroatom and/or being optionally substituted with at least one halogen and/or one hydroxyl radical;

$R^{46}$ and $R^{47}$, which may be identical or different, are chosen from a hydrogen atom and hydrocarbon chains chosen from saturated and unsaturated, linear, branched and cyclic chains containing from 10 to 16 carbon atoms, for example from 12 to 14 carbon atoms, in particular a saturated linear hydrocarbon chain; or 2) —A is a saturated hydrocarbon chain chosen from saturated, linear and branched hydrocarbon chains containing from 2 to 18 carbon atoms, for example 3 to 12 carbon atoms, optionally substituted with the substituents mentioned above, and/or optionally comprising at least one heteroatom and/or being optionally substituted with at least one halogen and/or one hydroxyl radical;

$R^{46}$ and $R^{47}$, which may be identical or different, are chosen from a hydrogen atom and a hydrocarbon chain chosen from saturated and unsaturated, linear, branched and cyclic hydrocarbon chains such as saturated linear hydrocarbon chains containing from 10 to 20 carbon atoms, for example from 11 to 18 carbon atoms, and in particular 16 carbon atoms; or alternatively 3) —A is chosen from aryl and aralkyl nuclei containing from 4 to 12 carbon atoms, for example from 5 to 8 carbon atoms, optionally substituted with the substituents mentioned above and/or optionally comprising at least one heteroatom and/or optionally substituted with at least one halogen and/or one hydroxyl radical;

$R^{46}$ and $R^{47}$, which may be identical or different, are chosen from a hydrogen atom and hydrocarbon chains chosen from saturated and unsaturated, linear, branched and cyclic hydrocarbon chains, for example a saturated linear hydrocarbon chain containing from 6 to 18 carbon atoms, for example from 10 to 16 carbon atoms.

A may be for example a divalent radical such as cyclohexylene, ethylene, propylene, isopropylene, butylene, isobutylene, pentylene, hexylene, dodecylene, dodecanylene, benzylene, phenylene, methylphenylene, bisphenylene or naphthalene.

The radicals $R^{46}$ and $R^{47}$ may be chosen, independently of each other, from pentyl, hexyl, decyl, undecyl, dodecyl, pentadecyl, hexadecyl, heptadecyl, octadecyl, 3-dodecyloxypropionyl, 3-octadecyloxypropionyl, 3-dodecyloxypentyl, 3-octadecyloxypentyl and 11-hydroxyheptadecyl radicals.

In one embodiment, $R^{46}$ and $R^{47}$ are identical.

When A is cyclic, the radicals $R^{46}$—CO—NH and $R^{47}$—CO—NH— may be in the ortho, meta or para position. Furthermore, they may be in the cis or trans position relative to each other.

In one embodiment, the compounds of formula (XIV) are a mixture of cis and trans compounds.

The compounds of formula (XIV) may be chosen from the compounds corresponding to one of the following formulae:

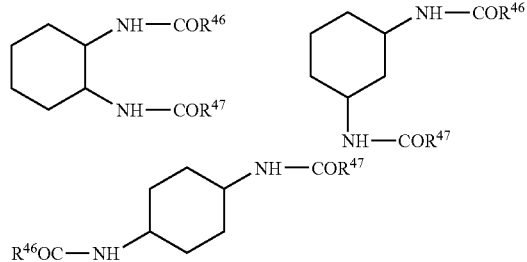

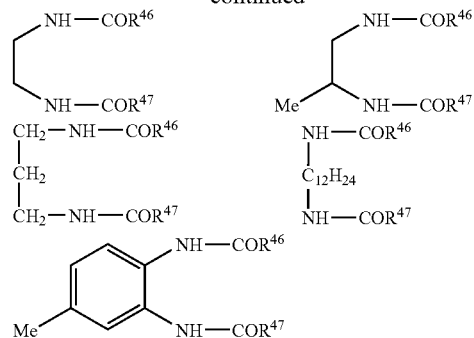

in which $R^{46}$ and $R^{47}$ are as defined above.

Among the compounds which may be used as organogelling agents in the composition of the invention, the following compounds may be mentioned:

N,N'-bis(dodecanoyl)-1,2-diaminocyclohexane, in particular in the trans form (compound of formula (XIV) with $R^{46}=R^{47}=n-C_{11}H_{23}$ and A=the divalent radical 1,2-cyclohexylene, also known as (2-dodecanoylaminocyclohexyl) dodecanamide). This compound is described in particular by Hanabusa K.; Angew. Chem., 108, 1997, 17, pages 2086-2088 [29];

N,N'-bis(dodecanoyl)-1,3-diaminocyclohexane, in particular in the trans form (compound of formula (XIV) with $R^{46}=R^{47}=n-C_{11}H_{23}$ and A=the divalent radical 1,3-cyclohexylene, also known as (3-dodecanoylaminocyclohexyl) dodecanamide), N,N'-bis(dodecanoyl)-1,4-diaminocyclohexane, in particular in the trans form (compound of formula (XIV) with $R^{46}=R^{47}=n-C_{11}H_{23}$ and A=the divalent radical 1,4-cyclohexylene, also known as (4-dodecanoylaminocyclohexyl) dodecanamide), N,N'-bis(dodecanoyl)-1,2-ethylenediamine, (compound of formula (XIV) with $R^{46}=R^{47}=n-C_{11}H_{23}$ and A=the divalent radical 1,2-ethylene, also known as (2-dodecanoylaminoethyl)dodecanamide), N,N'-bis(dodecanoyl)-1-methyl-1,2-ethylenediamine, (compound of formula (XIV) with $R^{46}=R^{47}=n-C_{11}H_{23}$ and A=the divalent radical 1-methyl-1,2-ethylene, also known as (2-dodecanoylamino-2-methylethyl)dodecanamide), N,N'-bis(dodecanoyl)-1,3-diaminopropane (compound of formula (XIV) with $R^{46}=R^{47}=n-C_{11}H_{23}$ and A=the divalent radical propylene, also known as (2-dodecanoylaminopropyl)dodecanamide), N,N'-bis(dodecanoyl)-1,12-diaminododecane (compound of formula (XIV) with $R^{46}=R^{47}=n-C_{11}H_{23}$ and A=the divalent radical 1,12-dodecylene, also known as (2-dodecanoylaminododecyl)dodecanamide), N,N'-bis(dodecanoyl)-3,4-diaminotoluene (compound of formula (XIV) with $R^{46}=R^{47}=n-C_{11}H_{23}$ and A=the divalent radical 1-methyl-3,4-phenylene, also known as (2-dodecanoylamino-4-methylphenyl)dodecanamide), and mixtures thereof.

The compounds of formula (XIV) may be prepared according to methods well known to persons skilled in the art.

In particular, they may be obtained by reacting a diamine $H_2N$-A-$NH_2$ with an acid chloride $R^{46}COCl$ and/or $R^{47}COCl$ where $R^{46}$ and $R^{47}$ have the meanings given above, in an organic solvent medium which is compatible for carrying out the reaction (1 mol of acid chloride is used per mol of diamine if it is desired to obtain a compound of formula (XIV) containing only one group $R^{46}$ other than a hydrogen atom, or 2 mol of acid chloride $R^{46}COCl$ and/or $R^{47}COCl$, if it is desired to obtain a compound of formula (XIV) in which $R^{46}$ and $R^{47}$ are different from a hydrogen atom). The reaction is preferably carried out in the presence of a base capable of neutralizing the formation of HCl released during the reaction. The diamide formed is extracted from the reaction medium according to extraction techniques which are well known to persons skilled in the art.

The compounds of formula (XIV) may be used, alone or in the form of a mixture, in the composition of the invention.

Standard Preparation of Compounds of Formula (XIV) with $R^{46}$=$R^{47}$

The diamine and two equivalents of triethylamine are dissolved in 50 ml of tetrahydrofuran (THF). Two equivalents of acyl chloride dissolved in THF are added and the reaction mixture is heated to the refluxing temperature of tetrahydrofuran, while monitoring the disappearance of the acyl chloride by infrared spectroscopy (typically for the majority in two hours). The precipitate is removed from the solution by filtration, the organic phase is concentrated and a liquid/liquid extraction is carried out on the solid compound obtained. The organic phase is then dried and then concentrated and the solid product obtained is recrystallized.

Organogelling Agents of Formula (XV):

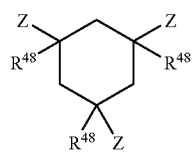

(XV)

in which the groups $R^{48}$, which are identical or different, are chosen from a hydrogen atom and saturated, linear and branched hydrocarbon chains, the said hydrocarbon chains containing from 1 to 6 carbon atoms, for example from 1 to 4 carbon atoms;

the groups Z, which are identical or different, each represent a group chosen from the following groups: —CO—S—$R^{49}$; —CO—NHR$^{49}$; —NH—COR$^{49}$ and —S—COR$^{49}$; in which the groups $R^{49}$, which may be identical or different, are chosen from:

a hydrogen atom, an aryl group, an aralkyl group, that is to say an aryl group substituted with a hydrocarbon chain chosen from saturated, linear and branched hydrocarbon chains, in which the hydrocarbon chain contains from 1 to 22 carbon atoms, for example from 10 to 18 carbon atoms, and a saturated hydrocarbon chain chosen from linear, branched and cyclic hydrocarbon chains, containing from 1 to 22 carbon atoms, for example from 10 to 18 carbon atoms, optionally substituted with at least one group chosen from aryl, ester, amide and urethane groups; and/or optionally comprising at least one heteroatom chosen from O, S and N; and/or optionally substituted with at least one fluorine atom and/or one hydroxyl radical.

$R^{48}$ is for example a hydrogen atom.

Z is for example the group —CO—NHR$^{49}$ or —NH—COR$^{49}$.

$R^{49}$ is for example an aryl group; an aralkyl group in which the linear or branched alkyl chain contains from 12 to 16 carbon atoms; or a linear or branched $C_{11}$-$C_{18}$ alkyl group.

In one embodiment, Z is a group —CO—NHR$^{49}$ in which $R^{49}$ is chosen from aryl groups substituted with a linear or branched $C_{11}$-$C_{16}$ alkyl chain, unsubstituted linear $C_{11}$ to $C_{18}$ alkyl chains and unsubstituted branched $C_{11}$ to $C_{18}$ alkyl chains.

In the compounds of formula (XV), the three substituents represented by Z may be in cis-cis, cis-trans or trans-trans conformation relative to each other. In particular, at least one of these substituents may be placed in an equatorial position on the cyclohexane nucleus; for example all the substituents Z are placed in an equatorial position.

It is also possible to use, as compound of formula (XV), a mixture of cis-cis, cis-trans and/or trans-trans compounds.

Among the compounds of formula (XV) which may be used as organogelling agent, alone or in the form of a mixture, in the composition of the invention, the following compounds may be mentioned:

cis-1,3,5-tris(dodecylaminocarbonyl)cyclohexane,
cis-1,3,5-tris(octadecylaminocarbonyl)cyclohexane,
cis-1,3,5-tris[N-(3,7-dimethyloctyl)aminocarbonyl]-cyclohexane,
trans-1,3,5-trimethyl-1,3,5-tris(dodecylaminocarbonyl)cyclohexane, and
trans-1,3,5-trimethyl-1,3,5-tris(octadecylaminocarbonyl)cyclohexane.

The compounds of formula (XV) are well known to persons skilled in the art and may be prepared by conventional methods.

It is also possible to add to the composition an organic compound as described in U.S. Pat. No. 6,156,325 [28]. Such compounds include urea urethanes having the following formula:

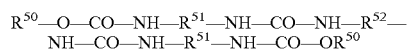

where $R^{50}$ represents $C_nH_{2n+1}$- or $C_mH_{2m+1}(C_pH_{2p}O)_r$; n represents an integer having a value of 4 to 22; m represents an integer having a value of 1 to 18; p represents an integer having a value of 2 to 4; and r represents an integer having a value of 1 to 10, $R^{51}$ represents:

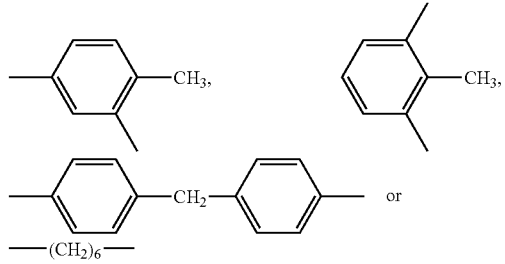

and $R^{52}$ represents:

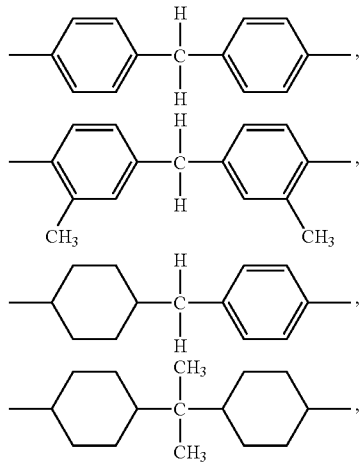

-continued

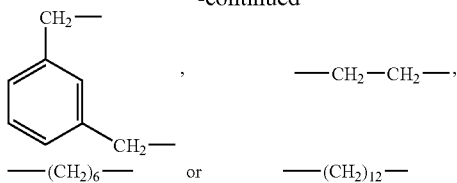, —CH$_2$—CH$_2$—,

—(CH$_2$)$_6$—   or   —(CH$_2$)$_{12}$—

As is evident from the above urea urethane formula, the alkyl groups and the alkyl parts designated for R$^{50}$ are saturated.

Organogelling Agent of Formula (XVI)

According to the invention, the organogelling agent may be at least one organogelling agent of formula (XVI):

$$R^{46}NHCONHANHCONHR^{46} \tag{XVI}$$

in which A and R$^{46}$ have the same meaning as that given for formula (XIV) given above, that is in which the groups R$^{46}$, which may be identical or different, each represent a hydrogen atom or a hydrocarbon chain chosen from saturated and unsaturated, linear, branched and cyclic hydrocarbon chains containing from 1 to 22 carbon atoms, for example from 6 to 18 carbon atoms, optionally substituted with at least one group chosen from aryl (—C$_6$H$_5$), ester (—COOR$^{48}$ where R$^{48}$ is as defined above), amide (—CONHR$^{48}$), urethane (—OCONHR$^{48}$) and urea (—NHCONHR$^{48}$) groups; and/or optionally containing from 1 to 3 heteroatoms chosen from O, S and N; and/or optionally substituted with 1 to 4 hydrogen atoms, in particular fluorine atoms, and/or 1 to 3 hydroxyl radicals, provided that at least one R$^{46}$ is other than a hydrogen atom, and A is chosen from saturated and unsaturated, linear, cyclic and branched hydrocarbon chains containing from 1 to 18 carbon atoms, for example from 2 to 12 carbon atoms, optionally substituted with at least one group chosen from aryl (—C$_6$H$_5$), ester (—COOR$^{48}$), amide (—CONHR$^{48}$), urethane (—OCONHR$^{48}$) and urea (—NHCONHR$^{48}$) groups; and/or optionally containing from 1 to 3 heteroatoms chosen from O, S and N; and/or optionally substituted with 1 to 4 halogen atoms such as fluorine atoms, and/or 1 to 3 hydroxyl radicals.

According to the invention, among the organogelling agents described above, those which can be carried in silicone oils and considered as gelling agents for these media when they are used alone, without the polymer of the invention, are preferred. They are the following compounds:

a) 12-hydroxystearic acid, its salts and its ester or amide derivatives which are described in the documents U.S. Pat. No. 5,480,637 [30], EP-A-616 842 [31] and EP-A-665 007 [32] as gelling agents for silicone oils.

b) amides of tricarboxylic acids, for example their diamides as described in U.S. Pat. No. 5,776,494 [33].

c) esters and amides of N-acylamino acids described in WO-A-93/23008 [15] and U.S. Pat. No. 5,429,816 [34], for example N-acylglutamides where the acyl group is a C$_8$ to C$_{22}$, and the dibutylamide of N-laurylglutamic acid from Ajinomoto.

d) diureas of N-acylamino acids such as the methyl or ethyl esters of N$^\epsilon$-lauroyl-N$^\alpha$stearylaminocarbonyl-L-lysine and of N$^\epsilon$-lauroyl-N$^\alpha$-n-butylamino-L-lysine of formulae:

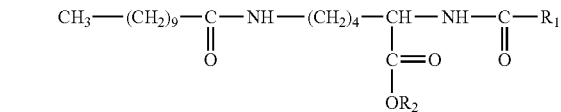

with R$_1$ = —NH—CH$_2$)$_{17}$—CH$_3$   or
—NH—(CH$_2$)$_3$—CH$_3$   and

R$_2$ = —CH$_3$   or   —C$_2$H$_5$,

These derivatives are described by K. Hanabusa, Chemistry Letters, 2000, pp. 1070-1071 [20].

e) Urethane amides of certain dipeptides such as N-benzyloxycarbonyl-L-valyl-L-valine n-octadecylamide of formula:

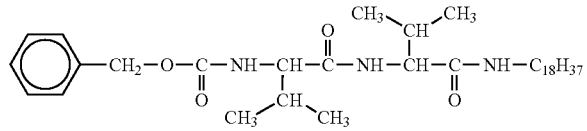

described by K. Hanabusa, J. Chem. Soc., Chem. Commun., 1993, pages 390-92 [35].

f) Dibenzylidenesorbitol and its derivatives.

g) Sterol derivatives such as:

the lanosterol described in EP-A-1 064 925 [36], dihydrolanosterol, cholesterol esters such as cholesterylphenyl acetate, cholesteryl laureate, cholesteryl cinnamate and cholesteryl 4-(2-anthryloxy)butanoate, and cholesterol esters with azobenzene groups such as:

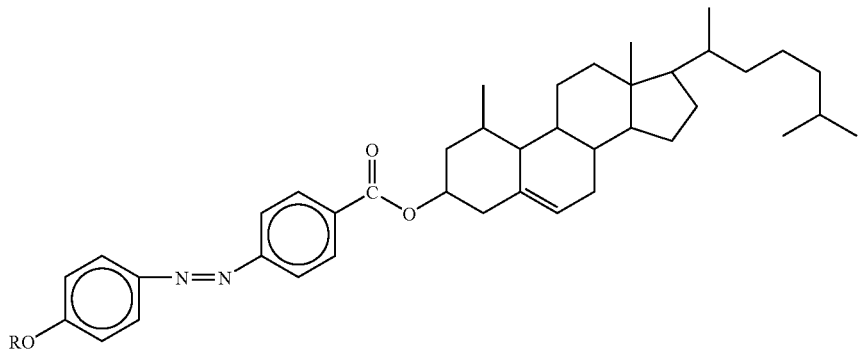

with   —OR =   —OMe,   —OEt,   —OPr,   —OBu,   —OPe,   —ODec described by P. Terech, Chem. Rev., 97, 3133-59, 1997 [37].

h) Certains cyclodipeptides cited in the article by K. Hanabusa, J. Colloïd and Int. Sci., 224, pp. 231-44, 2000 [38], in particular: cyclo(glycyl-L-alanyl), cyclo(glycyl-L-valyl), cyclo(glycyl-L-leucyl), cyclo(glycyl-L-phenylalanyl), cyclo (L-valyl-L-leucyl), cyclo(L-leucyl-L-leucyl), cyclo(L-phenylalanyl-L-leucyl), cyclo(L-phenylalanyl-L-phenylalanyl), cyclo(L-valyl-L-γ-3,7-dimethyloctylglutamyl), cyclo(L-valyl-L-γ-2-ethylhexylglutamyl), cyclo(L-leucyl-L-γ-ethylglutamyl), cyclo(L-leucyl-L-γ-dodecylglutamyl), cyclo(L-leucyl-L-γ-3,7-dimethyloctylglutamyl), cyclo(L-leucyl-L-γ-benzylglutamyl), cyclo(L-β-butylasparaginyl-L-phenylalanyl), cyclo(L-γ-dodecylasparaginyl-L-phenylalanyl), cyclo(L-β-3,7-dimethyloctylasparaginyl-L-phenylalanyl), cyclo(L-β-2-ethylhexylasparaginyl-L-phenylalanyl), cyclo(L-β-3,5,5-trimethylhexylasparaginyl-L-phenylalanyl) and cyclo(L-β-2-ethylbutylasparaginyl-L-phenylalanyl).

i) the trans-(1R,2R)-bis(undecylcarbonylamino)-cyclohexane derivative of formula:

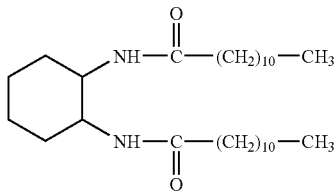

j) Fluorinated ethers such as those defined in U.S. Pat. No. 6,002,048 [39].

k) The organogelling agents defined in WO 01/07007 [16], of general formula (XVII) described above.

l) The bolaamphiphilic amide organogelling agents derived from amino acids mentioned above.

m) The 2-alkyl-2-ammoniumisobutyl acetate p-toluenesulfonate salts of formula (XXII) cited above, in particular that for which $R^{37}$ is derived from L-leucine and $R^{38}$ represents —$(CH_2)_{11}CH_3$.

n) The diamide derivatives of benzenedicarboxylic acid and of valine cited above.

o) The non-polymeric organogelling agents of formula (XXV) or (XXVI) described above.

Among the preferred organogelling agents, the ones which will be even more preferred are those which are compatible with silicone oils and which in addition possess groups which can give hydrogen interactions with the polyorganosiloxane polymers used in the invention, that is amide, urea, urethane, ester, sulfonamide, carbamate, thiocarbamate, thiourea, oxamido, guanidino and biguanidino groups, and combinations thereof.

In a particularly preferred manner, there will be used in accordance with the invention:

12-hydroxystearic acid amide derivatives,
amides of tricarboxylic acids,
esters or amides of N-acylamino acids,
the diureas cited above,
urethane amides of certain dipeptides,
the cyclodipeptides cited above,
the derivatives of formula (XIV) and more particularly trans-(1R,2R)-bis(undecylcarbonylamino)cyclohexane,
bolaamphipilic amide organogelling agents derived from amino acids,
diamide derivatives of benzenedicarboxylic acid and of valine, and
organogelling agents which are soluble in silicone oils and which have a non-polymeric structure, defined by the formulae XXV and XXVI given above.

According to the invention, the polymer may be combined with at least one amphiphilic compound which is liquid at room temperature, having a hydrophilic/lipophilic balance (HLB) value of less than 12, in particular ranging from 1 to 7, preferably from 1 to 5, and even better from 3 to 5. According to the invention, it is possible to use one or more amphiphilic compounds. The aim of these amphiphilic compounds is to reinforce the structuring properties of the polymer, to facilitate the use of the polymer and to enhance the capacity of the stick to form a deposit.

According to the invention, the composition preferably has a hardness ranging from 20 to 2 000 gf and better still from 20 to 900 gf, particularly from 20 to 600 gf, and for example from 150 to 450 gf. This hardness may be measured according to a method of penetration of a probe into the said composition and in particular with the aid of a texture analyser (for example TA-TXT2i from Rheo) equipped with an ebonite cylinder 25 mm in height and 8 mm in diameter. The hardness measurement is carried out at 20° C. at the centre of five samples of the said composition. The cylinder is introduced into each sample of composition at a pre-speed of 2 mm/s, then at a speed of 0.5 mm/s and finally at a post-speed of 2 mm/s, the total displacement being 1 mm. The recorded hardness value is that of the maximum peak. The measurement error is ±50 gf.

The hardness may also be measured by the "cheese wire" method, which consists in cutting a tube of lipstick 12.7 mm or 8.1 mm in diameter and in measuring the hardness at 20° C., using a DFGHS 2 tensile testing machine from the company Indelco-Chatillon, travelling at a speed of 100 mm/minute. It is expressed as the shear force (expressed in gram-force) required to cut a stick under these conditions. According to this method, the hardness of a composition in stick form according to the invention ranges from 30 to 300 gf, preferably from 30 to 250 gf, for a stick 12.7 mm in diameter and for example from 30 to 120 gf for a stick 8.1 mm in diameter.

The hardness of the composition according to the invention is such that the composition is self-supporting and can disintegrate easily to form a satisfactory deposit on the skin and the lips. In addition, with this hardness, the composition of the invention shows good impact strength.

According to the invention, the composition in stick form has the behaviour of a deformable and supple elastic solid, giving noteworthy elastic softness on application. The stick compositions of the prior art do not have this property of elasticity and suppleness.

The amphiphilic, silicone and non-silicone compound(s) which can be used in the composition of the invention comprise a lipophilic part linked to a polar part, the lipophilic part containing a carbon chain having at least 8 carbon atoms, in particular from 18 to 32 carbon atoms and even better from 18 to 28 carbon atoms. Preferably, the polar part of this or these amphiphilic compound(s) is the residue of a compound chosen from alcohols and polyols having from 1 to 12 hydroxyl groups, polyoxyalkylenes containing at least two oxyalkylenated moieties and having from 0 to 20 oxypropylenated moieties and/or from 0 to 20 oxyethylenated moieties. In particular, the amphiphilic compound is an ester chosen from hydroxystearates, oleates and isostearates of glycerol, sorbitan or methylglucose, or branched $C_{12}$ to $C_{26}$ fatty alcohols such as octyldodecanol and mixtures thereof. Among these esters, monoesters and mixtures of mono- and diesters are preferred.

The respective amounts of lipophilic non-polymeric organogelling agent and of structuring silicone polymer and optionally of amphiphilic compound are chosen according to the desired gel hardness and depending on the particular application envisaged. The respective quantities of polymer, organogelling agent and optionally of amphiphilic compound should be such that they allow the production of a self-supported composition, for example in the form of a disintegrable stick. In practice, the quantity of polymer (as active material) represents from 0.5 to 80% of the total weight of the composition, and even better from 5 to 40%. The quantity of amphiphilic compound represents in practice from 0.1% to 35% of the total weight of the composition, for example from 1% to 20% and even better from 2% to 15%. The quantity of organogelling agent represents in practice from 0.1 to 80%, preferably from 0.5 to 60%, and even better from 1 to 40% and better still from 1 to 15% of the total weight of the composition.

According to the invention, it is in fact preferable for the quantity of organogelling agent to be smaller than the quantity of structuring silicone polymer.

Generally, the silicone polymer/non-polymeric organogelling agent mass ratio is in the range from 20 to 0.15, preferably from 15 to 1.5.

Other Additives

The composition of the invention may also comprise any ingredient usually used in the field under consideration, and especially those chosen from dyes that are soluble in polyols or in the fatty phase, antioxidants, essential oils, preserving agents, perfumes, liposoluble polymers, especially hydrocarbon-based liposoluble polymers such as polyalkylenes or polyvinyl laurate, liquid-fatty-phase gelling agents, waxes, gums, resins, surfactants, for instance trioleyl phosphate, additional cosmetic or dermatological active agents such as, for example, water, emollients, moisturizers, vitamins, liquid lanolin, essential fatty acids, lipophilic sunscreens or sunscreens that are soluble in polyols, and mixtures thereof. The composition according to the invention may also contain lipid vesicles of ionic and/or non-ionic type. These ingredients, besides the water, may be present in the composition in the usual manner in a proportion of from 0% to 20% of the total weight of the composition and better still from 0.1% to 10%.

In the case where the composition contains an aqueous phase, which is the case for a simple or multiple emulsion, this aqueous phase can represent 0.1% to 70% of the total weight of the composition, especially from 0.5% to 40% and better still from 1% to 20%. This aqueous phase can contain any water-miscible compound such as polyols and may be optionally gelled with a suitable gelling agent.

Needless to say, the person skilled in the art will take care to select the optional additional ingredients and/or the amount thereof such that the advantageous properties of the composition according to the invention are not, or are not substantially, adversely affected by the envisaged addition.

The compositions of the invention may in particular contain one or more waxes, for example polyethylene wax, but the use of wax is avoided if it is desired to obtain glossy, or even transparent products. Generally, the amount of wax does not exceed 20% and preferably 10%; it represents, for example, from 3% to 5% of the total weight of the composition.

The composition according to the invention may be in the form of an optionally tinted dermatological or care composition for keratinous materials such as the skin, the lips and/or the superficial body growths, in the form of a sun protection or care composition, especially in the form of a make-up-removing product in stick form. It can especially be used as a care base for the skin, the superficial body growths or the lips (lip balms, for protecting the lips against the cold and/or sunlight and/or the wind, or a care cream for the skin, the nails or the hair).

The composition of the invention may be provided in particular in the form of a rigid gel, in particular in the form of a transparent anhydrous stick.

The composition of the invention may also be in the form of a coloured make-up product for the skin, in particular a foundation, optionally having care or treatment properties, a blusher, a face powder, an eyeshadow, a concealer product, an eyeliner or a make-up product for the body; a lip make-up, for instance a lipstick, optionally having care or treatment properties; a make-up for the superficial body growths, for instance the nails or the eyelashes, in particular in the form of a mascara cake, or for the eyebrows and the hair, especially in the form of a pencil. In particular, the composition of the invention may be a cosmetic product containing cosmetic and/or dermatological active agents, for instance essential oils, vitamins, moisturizers, sunscreens, cicatrizing agents and ceramides.

In the case of make-up compositions, hydrophobic or hydrophilic solid particles may constitute the pigment(s) for making up the skin, the lips and/or the superficial body growths.

Needless to say, the composition of the invention must be cosmetically or dermatologically acceptable, that is to say that it must contain a non-toxic physiologically acceptable medium that can be applied to the skin, the superficial body growths or the lips of human beings. For the purposes of the invention, the expression "cosmetically acceptable" means a composition of pleasant appearance, odour and feel.

Moreover, the make-up or care compositions in accordance with the invention must comprise at least 10% by mass of a non-volatile oil (silicone oil or non-silicone oil) and/or of a pasty or viscous product in order to obtain a product which is comfortable and which does not cause tightness.

The expression pasty product is understood to mean a viscous fatty substance containing a liquid fraction and a solid fraction. For the purposes of the invention, the expression "pasty fatty substances" means fatty substances with a melting point ranging from 20 to 55° C. and preferably 25 to 45° C., and/or a viscosity at 40° C. ranging from 0.1 to 40 Pa·s (1 to 400 poises) and preferably 0.5 to 25 Pa·s measured using a Contraves TV or Rheomat 180 viscometer, equipped with a spindle rotating at 240 $min^{-1}$ for a power supply at 60 Hz or at 200 $min^{-1}$ for a power supply at 50 Hz.

A person skilled in the art can select the spindle for measuring the viscosity, from the spindles MS-r3 and MS-r4, on the basis of his general knowledge, so as to be able to measure the viscosity of the tested pasty compound.

The melting point values correspond, according to the invention, to the melting peak measured by the "Differential Scanning Calorimetry" method with a temperature rise of 5 or 10° C./min.

By way of example of pasty products that may be used in the invention, mention may be made of lanolins and lanolin derivatives, for instance acetylated lanolins or oxypropylenated lanolins or isopropyl lanolate, with a viscosity of 18 to 21 Pa·s and preferably 19 to 20.5 Pa·s, and/or a melting point of 30 to 55° C., preferably 30 to 40° C., and mixtures thereof. Esters of fatty acids or of fatty alcohols may also be used, especially those containing 20 to 65 carbon atoms (melting point of about 20 to 35° C. and/or viscosity at 40° C. ranging from 0.1 to 40 Pa·s), for instance triisostearyl citrate or cetyl citrate; arachidyl propionate; polyvinyl laurate; cholesterol esters, for instance triglycerides of plant origin such as hydrogenated plant oils, viscous polyesters, for instance poly(12-hydroxystearic acid) and mixtures thereof. Triglycerides of plant origin that may be used include hydrogenated castor oil derivatives, such as "THIXINR" from Rheox.

Mention may also be made of silicone-based pasty fatty substances such as polydimethylsiloxanes (PDMSs) containing pendent chains of the alkyl or alkoxy type containing from 8 to 24 carbon atoms, and having a melting point of 20-55° C., for example 20 to 40° C., for instance stearyl dimethicones, especially those sold by the company Dow Corning under the trade names DC2503 and DC25514, and mixtures thereof.

The pasty fatty substance(s) may be present in a proportion of from 0 to 60% by weight relative to the total weight of the composition, preferably in a proportion of 0.1-45% by weight and even more preferably in a proportion of 2-30% by weight.

According to the invention, the composition may furthermore contain colouring matter which may be a pigment or a pearlescent agent as defined above, or a soluble compound chosen from lipophilic dyes, hydrophilic dyes, and mixtures thereof.

The liposoluble dyes are, for example, Sudan red, DC Red 17, DC Green 6, β-carotene, soybean oil, Sudan brown, DC Yellow 11, DC Violet 2, DC Orange 5, quinoline yellow and annatto. The hydrophilic dyes are for example beet juice and methylene blue. Each type of dye can represent from 0% to 20% of the weight of the composition and better still from 0.1% to 6% (if present).

The composition according to the invention may be manufactured by known methods, generally used in the cosmetic or dermatological field. It may be manufactured by the method which consists in heating the polymer at least to its softening point, adding thereto the pasty compounds and/or the optional waxes, the oil(s), the organogelling agent, if necessary the amphiphilic compound(s), the colouring matter and/or the solid particles, and the additives, and then in mixing the whole until a transparent, clear solution is obtained. The homogeneous mixture obtained can then be cast in a suitable mould such as a lipstick mould, or directly into the packaging articles (especially a case or dish).

The subject of the invention is also a make-up structured solid composition for the skin, the lips and/or the superficial body growths, containing at least one pigment in a sufficient quantity for applying make-up to the skin, the lips and/or the superficial body growths and a liquid continuous fatty phase comprising at least one silicone oil structured with at least one polymer (homopolymer or copolymer) having a weight-average molecular mass ranging from 500 to 500 000, containing at least one moiety comprising:
  at least one polyorganosiloxane group, consisting of 1 to 1 000 organosiloxane units in the chain of the moiety or in the form of a graft, and
  at least two groups capable of establishing hydrogen interactions chosen from ester, amide, sulphonamide, carbamate, thiocarbamate, urea, thiourea, oxamido, guanidino and biguanidino groups, and combinations thereof, provided that at least one group is different from an ester group, the polymer being solid at room temperature and soluble in the liquid fatty phase at a temperature of 25 to 250° C., the liquid fatty phase consisting partially or totally of silicone oil(s) and containing a non-polymeric organogelling agent, the said composition being provided in the form of a solid, and the pigment, the liquid fatty phase, the organogelling agent and the polymer forming a physiologically acceptable medium.

This make-up composition is preferably self-supporting.

The subject of the invention is also a lipstick structured composition, containing at least one pigment in a sufficient quantity for applying make-up to the lips and a liquid continuous fatty phase comprising at least one silicone oil structured with at least one polymer (homopolymer or copolymer) having a weight-average molecular mass ranging from 500 to 500 000, containing at least one moiety comprising:
  at least one polyorganosiloxane group, consisting of 1 to 1 000 organosiloxane units in the chain of the moiety or in the form of a graft, and
  at least two groups capable of establishing hydrogen interactions chosen from ester, amide, sulphonamide, carbamate, thiocarbamate, urea, thiourea, oxamido, guanidino and biguanidino groups, and combinations thereof, provided that at least one group is different from an ester group, the polymer being solid at room temperature and soluble in the liquid fatty phase at a temperature of 25 to 250° C., the liquid fatty phase consisting partially or totally of silicone oil(s) and of an organogelling agent, the said composition being provided in the form of a solid, and the pigment, the liquid fatty phase and the polymer forming a physiologically acceptable medium.

The composition of the invention may be provided in the form of a cake mascara, an eyeliner, a foundation, a lipstick, a blusher, a make-up-removing product, a make-up product for the body, an eyeliner or a face powder, or a concealer product.

The subject of the invention is also a make-up stick for the skin, the lips and/or the superficial body growths, and in particular for the lips, containing at least one pigment in a sufficient quantity for applying make-up to the skin, the lips and/or the superficial body growths and a liquid continuous fatty phase comprising at least one silicone oil structured with at least one polymer (homopolymer or copolymer) having a weight-average molecular mass ranging from 500 to 500 000, containing at least one moiety comprising:
  at least one polyorganosiloxane group, consisting of 1 to 1 000 organosiloxane units in the chain of the moiety or in the form of a graft, and
  at least two groups capable of establishing hydrogen interactions chosen from ester, amide, sulphonamide, carbamate, thiocarbamate, urea, thiourea, oxamido, guanidino and biguanidino groups, and combinations thereof, provided that at least one group is different from an ester group, the polymer being solid at room temperature and soluble in the liquid fatty phase at a temperature of 25 to 250° C., the liquid fatty phase consisting partially or totally of silicone oil(s) and of organogelling agent, the pigment, the fatty phase and the polymer forming a physiologically acceptable medium.

The invention relates to a cosmetic care, make-up or treatment method for the keratinous materials of human beings, comprising the application to the keratinous materials of a cosmetic composition in accordance with the invention.

The subject of the invention is also the use of a sufficient quantity of at least one polymer (homopolymer or copolymer) having a weight-average molecular mass ranging from 500 to 500 000, containing at least one moiety comprising:

at least one polyorganosiloxane group, consisting of 1 to 1 000 organosiloxane units in the chain of the moiety or in the form of a graft, and at least two groups capable of establishing hydrogen interactions chosen from ester, amide, sulphonamide, carbamate, thiocarbamate, urea, thiourea, oxamido, guanidino and biguanidino groups, and combinations thereof, provided that at least one group is different from an ester group, the polymer being solid at room temperature and soluble in the liquid fatty phase at a temperature of 25 to 250° C., in a cosmetic composition or for the manufacture of a physiologically acceptable composition, containing a liquid continuous fatty phase comprising at least one silicone oil, the liquid fatty phase consisting partially or totally of silicone oil(s) having a flash point equal to or greater than 40° C. and greater than the softening point of the polymer and containing an organogelling agent, to structure the said composition in the form of a self-supporting solid with a hardness ranging from 20 to 2 000 gf and preferably from 20 to 900 gf and even better from 20 to 600 gf.

The subject of invention is also the use of a continuous liquid fatty phase comprising at least one silicone oil, essentially structured with a sufficient quantity of at least one polymer (homopolymer or copolymer) having a weight-average molecular mass ranging from 500 to 500 000, containing at least one moiety comprising:

at least one polyorganosiloxane group, consisting of 1 to 1 000 organosiloxane units in the chain of the moiety or in the form of a graft, and at least two groups capable of establishing hydrogen interactions chosen from ester, amide, sulphonamide, carbamate, thiocarbamate, urea, thiourea, oxamido, guanidino and biguanidino groups, and combinations thereof, provided that at least one group is different from an ester group, the polymer being solid at room temperature and soluble in the liquid fatty phase at a temperature of 25 to 250° C., the liquid fatty phase consisting partially or totally of volatile oil(s) having a flash point equal to or greater than 40° C. and greater than the softening point of the polymer and containing an organogelling agent, in a cosmetic composition or for the manufacture of a physiologically acceptable, rigid, self-supporting, glossy and/or non-migrating composition, on the condition that the composition comprises at least 10% by mass of a non-volatile oil and/or of a pasty or viscous product.

The subject of the invention is also the use of a sufficient quantity of at least one polymer (homopolymer or copolymer) having a weight-average molecular mass ranging from 500 to 500 000, containing at least one moiety comprising:

at least one polyorganosiloxane group, consisting of 1 to 1 000 organosiloxane units in the chain of the moiety or in the form of a graft, and at least two groups capable of establishing hydrogen interactions chosen from ester, amide, sulphonamide, carbamate, thiocarbamate, urea, thiourea, oxamido, guanidino and biguanidino groups, and combinations thereof, provided that at least one group is different from an ester group, the polymer being solid at room temperature and soluble in the liquid fatty phase at a temperature of 25 to 250° C., in a cosmetic composition or for the manufacture of a physiologically acceptable composition, containing a liquid continuous fatty phase comprising at least one silicone oil and at least one organogelling agent, to structure the said composition in the form of a self-supporting solid.

The subject of the invention is also the use of a continuous liquid fatty phase comprising at least one silicone oil, essentially structured with a sufficient quantity of at least one polymer (homopolymer or copolymer) having a weight-average molecular mass ranging from 500 to 500 000, containing at least one moiety comprising:

at least one polyorganosiloxane group, consisting of 1 to 1 000 organosiloxane units in a chain of the moiety or in the form of a graft, and at least two groups capable of establishing hydrogen interactions chosen from ester, amide, sulphonamide, carbamate, thiocarbamate, urea, thiourea, oxamido, guanidino and biguanidino groups, and combinations thereof, provided that at least one group is different from an ester group, the polymer being solid at room temperature and soluble in the liquid fatty phase at a temperature of 25 to 250° C., the liquid fatty phase consisting partially or totally of volatile oil(s) having a flash point equal to or greater than 40° C. and greater than the softening point of the gelling polymer and containing an organogelling agent, in a cosmetic composition or for the manufacture of a physiologically acceptable composition, as agent for limiting the migration of the said composition, on the condition that the composition comprises at least 10% by mass of a non-volatile oil and/or of a pasty or viscous product.

According to an advantageous characteristic of these uses, the composition has a hardness of 20 to 2 000 gf, preferably of 20 to 900 gf and even better of 20 to 600 gf.

The invention finally relates to a cosmetic method for limiting the migration of a cosmetic composition containing a liquid fatty phase comprising at least one silicone oil, consisting in structuring the said fatty phase with a sufficient quantity of at least one polymer (homopolymer or copolymer) having a weight-average molecular mass ranging from 500 to 500 000, containing at least one moiety comprising:

at least one polyorganosiloxane group, consisting of 1 to 1 000 organosiloxane units in the chain of the moiety or in the form of a graft, and at least two groups capable of establishing hydrogen interactions chosen from ester, amide, sulphonamide, carbamate, thiocarbamate, urea, thiourea, oxamido, guanidino and biguanidino groups, and combinations thereof, provided that at least one group is different from an ester group, the polymer being solid at room temperature and soluble in the liquid fatty phase at a temperature of 25 to 250° C., the liquid fatty phase consisting partially or totally of silicone oil(s) and containing at least one organogelling agent.

DETAILED DISCLOSURE OF THE INVENTION

The invention is illustrated in greater detail in the following examples of make-up formulation. The quantities are given as % by mass. The chemical compounds are given mainly as the CTFA ("International Cosmetic Ingredient Dictionary") name. The viscosities are measured at 25° C. and at atmospheric pressure.

Example 1

Lipstick

| Composition | |
|---|---|
| Cyclopentasiloxane D5 | qs 100% |
| Phenyltrimethicone (DC 556 from Dow Corning, of 20 cSt) | 5% |
| Hydrogenated isoparaffin (Parleam ® from Nippon Oil Fats) | 5% |
| Hydrophobic treated pigments (red and yellow iron oxides and titanium oxide) | 10% |
| Silicone polyamide of Example 1 of U.S. Pat. No. 5,981,680 | 15% |
| Preservative qs | |
| Organogelling agent (dibutylamide of N-laurylglutamic acid) | 5% |
| Perfume qs | |

The pigments have the following colour indices (CI):
red iron oxide CI: 77491
yellow iron oxide CI: 77492
titanium oxide CI: 77891

This lipstick is obtained by heating the organogelling agent and the polymer until the whole melts, followed by addition of the Parleam and of a portion of the phenyltrimethicone. In parallel, the pigments and the other portion of the phenyltrimethicone are mixed at room temperature and then they are ground in a three-roll mill. This ground material is added to the molten mixture of wax and of silicone oils, and then the whole is homogenized. The whole is cooled by at least 20° C. relative to the melting point of the mixture and the cyclopentasiloxane D5 is then added, followed by the preservative and the perfume, still with stirring. The mixture is then cast in a suitable mould.

The product thus obtained has properties of staying power, in particular of the colour, of slipperiness and of non-greasiness.

Example 2

Foundation

| Composition | |
|---|---|
| Cyclopentasiloxane D5 | qs 100% |
| PDMS α-ω oxyethylenated/oxypropylenated in cyclopentasiloxane D5 (Abil EM 90 from Goldschmmitd) | 3% |
| Phenyltrimethicone (DC 556 from Dow Corning, of 20 cSt) | 5% |
| Hydrogenated isoparaffin (Parleam ® from Nippon Oil Fats) | 5% |
| Hydrophobic treated pigments (red and yellow iron oxides and titanium oxide) | 10% |
| Silicone polyamide of Example 2 of U.S. Pat. No. 5,981,680 | 15% |
| Preservative qs | |
| Organogelling agent[1] | 2% |
| Perfume qs | |

1) The organogelling agent is a cis-trans mixture of the compound of formula:

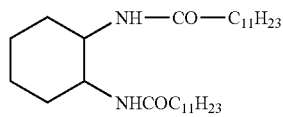

The pigments have the following colour indices (CI):
red iron oxide CI: 77491
yellow iron oxide CI: 77492
brown iron oxide CI: 77491
titanium oxide CI: 77891

This foundation is obtained by heating the organogelling agent and the polymer in the mixture of oils until the whole melts, followed by addition of the Parleam and of a portion of the phenyltrimethicone. In parallel, the pigments, Abil EM 90 and the other portion of the phenyltrimethicone are mixed at room temperature and then they are ground in a three-roll mill. This ground material is added to the molten mixture of wax and of silicone oils, and then the whole is homogenized by means of magnetic stirring. The whole is cooled by at least 20° C. relative to the melting point of the mixture and the cyclopentasiloxane D5 is then added, followed by the preservative and the perfume, still with stirring. The mixture is then cast in a suitable mould.

The product thus obtained has properties of staying power, in particular of the colour, of slipperiness and of non-greasiness.

Example 3

Anhydrous Foundation

| Composition | |
|---|---|
| PDMS (5 cSt) | qs 100% |
| Phenyltrimethicone (DC 556) | 5% |
| PDMS (300 cSt) | 5% |
| Hydrophobic treated pigments (red and yellow iron oxides and titanium oxide, treated with perfluoroalkyl phosphate) | 10% |
| Silicone polyamide of Example 2 of U.S. Pat. No. 5,981,680 | 12% |
| Hydrophobic treated silica (trimethylsiloxyl treatment) | 3% |
| Preservative qs | |
| Organogelling agent[1] | 4% |
| Perfume qs | |

[1]The organogelling agent is a cis-trans mixture of the compound of formula:

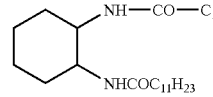

This foundation is prepared like the lipstick of Example 1, the silica being introduced at the same time as the phenyltrimethicone into the pigmented ground material and the isononyl isononanoate being introduced into the mixture of wax and of silicone oils.

It has properties of non-greasiness, slipperiness, mattness and good staying power over time, in particular of the colour.

The particles used are hydrophobic (or even better lipophilic) particles.

REFERENCES

[1] EP-A-1 068 856
[2] WO-A-01/97758
[3] U.S. Pat. No. 5,874,069
[4] U.S. Pat. No. 5,919,441
[5] U.S. Pat. No. 6,051,216
[6] WO-A-02/17870
[7] WO-A-02/17871
[8] EP-A-1 177 784
[9] U.S. Pat. No. 5,412,004

[10] EP-A-1 048 686
[11] U.S. Pat. No. 5,981,680
[12] Article by D. Robb, 1997, pp. 209-263, chapter 8 and by P. Terech "Specialist Surfactants"
[13] FR-A-2 796 276
[14] FR-A-2 811 552
[15] WO-93/23008
[16] WO-A-01/07007
[17] Article by R. J. H. Hafkamp, Chem. Commun., 1997, pages 545-546
[18] Article J. Org. Chem., vol. 64, No. 2, 412-26 (1999)
[19] Article by M. Jokic, J. Chem. Soc., Chem. Commun., pages 1723-24 (1995)
[20] Article by K. Hanabusa, Chemistry Letters, pp. 1070-71, 2000
[21] Article by K. Hanabusa, Chemistry Letters, pp. 767-8, 1999
[22] Article by X. Luo, Chem. Commun., pp. 2091-92, 2000
[23] Article by T. Shimizu, J. Am. Chem. Soc., 119, pp. 2812-18, 1997
[24] Article by K. Hanabusa, Adv. Mater., 9, No. 14, 1997, pp. 1095-1097
[25] Article by K. Hanabusa, Colloïd Polym. Sci., 276, pp. 252-59, 1998
[26] WO-A-00/61080
[27] WO-A-00/61081
[28] U.S. Pat. No. 6,156,325
[29] Article by K. Hanabusa, Agnew. Chem., 108, 1997, 17, pp. 2086-2088
[30] U.S. Pat. No. 5,480,637
[31] EP-A-616 842
[32] EP-A-665 007
[33] U.S. Pat. No. 5,776,494
[34] U.S. Pat. No. 5,429,816
[35] Article by K. Hanabusa, J. Chem. Soc., Chem. Commun., 1993, pp. 390-92
[36] EP-A-1 064 925
[37] Article by P. Terech, Chem. Rev., 97, 3133-59, 1997
[38] Article by K. Hanabusa, J. Colloïd and Int. Sci., 224, pp. 231-44, 2000
[39] U.S. Pat. No. 6,002,048
[40] WO-A-99/06473
[41] U.S. Pat. No. 6,353,076

The invention claimed is:

1. Care and/or make-up cosmetic composition comprising a liquid fatty phase comprising at least one volatile silicone oil and at least one volatile non-silicone oil, structured with a gelling system comprising:

1) at least one nylon 611/dimethicone copolymer,
2) at least one non-polymeric organogelling agent, wherein the organogelling agent is selected from the group consisting of:
   (1) —N,N'-bis(dodecanoyl)-1,2-diaminocyclohexane,
   (2) —N,N'-bis(dodecanoyl)-1,3-diaminocyclohexane,
   (3) —N,N'-bis(dodecanoyl)-1,4-diaminocyclohexane,
   (4) —N,N'-bis(dodecanoyl)-1,2-ethylenediamine,
   (5) —N,N'-bis(dodecanoyl)-1-methyl-1,2-ethylenediamine,
   (6) —N,N'-bis(dodecanoyl)-1,3-diaminopropane,
   (7) —N,N'-bis(dodecanoyl)-1,12-diaminododecane,
   (8) —N,N'-bis(dodecanoyl)-3,4-diaminotoluene,
   (9) —at least one compound chosen from the compounds of formula (XV):

in which the groups $R^{48}$, which are identical or different, are chosen from a hydrogen atom and saturated, linear and branched hydrocarbon chains, the said hydrocarbon chains containing from 1 to 6 carbon atoms;

the groups Z, which are identical or different, each represent a group chosen from the following groups: —CO—S—$R^{49}$; —CO—NHR$^{49}$; —NH—COR$^{49}$ and —S—COR$^{49}$; in which the groups $R^{49}$, which may be identical or different, are chosen from:

a hydrogen atom,
aryl groups,
aralkyl groups, and
saturated hydrocarbon chains chosen from linear, branched and cyclic hydrocarbon chains, containing from 1 to carbon atoms, optionally substituted with at least one group chosen from aryl, ester, amide and urethane groups; and/or optionally comprising at least one heteroatom chosen from O, S and N; and/or optionally substituted with at least one fluorine atom and/or one hydroxyl radical,

(10) —sterol derivatives selected from the group consisting of lanosterol, dihydrolanosterol, and cholesterol esters,

(11) —diamides of formula (XXV) or (XXVI):

or

in which the groups $R^{44}$, which may be identical or different, represent a saturated, linear or branched $C_8$-$C_{60}$ hydrocarbon chain, the group(s) $R^{44}$ optionally comprising a hydroxyl group or at least one heteroatom such as N, O, S or Si, $R^{45}$ is a hydrocarbon-based group chosen from linear, branched and cyclic $C_1$ to $C_{50}$ groups and $C_5$ to $C_8$ arylene groups optionally substituted with one or more $C_1$-$C_4$ alkyl groups, and X represents —O— or —NH—, and mixtures thereof, and

(12) —trans-(1R,2R)-bis(undecylcarbonylamino)cyclohexane of formula:

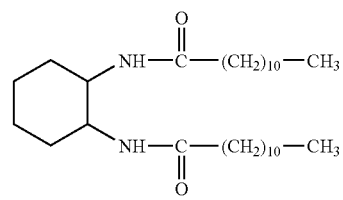

the liquid fatty phase and the gelling system forming a physiologically acceptable medium, and 3) at least one pigment in an amount sufficient to provide a coloring effect to keratin materials upon application.

2. Composition according to claim 1, in which the volatile silicone oil has a flash point equal to or greater than 40° C. and greater than the softening point of the gelling system.

3. Composition according to claim 1, in which the volatile silicone oil is chosen from the group consisting of the following compounds: octyltrimethicone, hexyltrimethicone, octamethylcyclotetrasiloxane D4, dodecamethylcyclohexasiloxane D6, heptamethyloctyltrisiloxane, decamethyltetrasiloxane, dodecamethylpentasiloxane, polydimethylsiloxane of 1.5 cSt, polydimethylsiloxane of 2 cSt, polydimethylsiloxane of 3 cSt, polydimethylsiloxane of 5 cSt, and mixtures thereof.

4. Composition according to claim 1, in which the volatile silicone oil has a flash point of 40 to 135° C.

5. Composition according to claim 1, in which the liquid fatty phase contains at least 30% silicone oil with respect to the total weight of the composition.

6. Composition according to claim 1, in which the volatile silicone oil represents from 3 to 89.4% of the total weight of the composition.

7. Composition according to claim 1, further comprising at least one filler comprising solid particles.

8. Composition according to claim 7, in which the solid particles are hydrophobic particles.

9. Composition according to claim 8, in which the solid particles are hydrophilic particles, coated with a film of hydrophobic compound.

10. Composition according to claim 7, in which the solid particles are hydrophilic particles and the composition further comprises an amphiphilic silicone.

11. Composition according to claim 1, in which the at least one pigment is chosen from zinc oxides, iron oxides, titanium oxides and mixtures thereof.

12. Composition according to claim 1, in which the at least one nylon 611/dimethicone copolymer represents from 0.5 to 80% of the total weight of the composition.

13. Composition according to claim 1, in which the liquid fatty phase further contains a non-volatile non-silicone oil.

14. Composition according to claim 1, in which the liquid fatty phase represents from 5 to 99% of the total weight of the composition.

15. Composition according to claim 1, in which in the at least one volatile non-silicone oil is at least one selected from the group consisting of isododecane, isohexadecane, isohexyl neopentanoate, and isodecyl neopentanoate.

16. Composition according to claim 1, in which in the at least one volatile non-silicone oil is at least one selected from the group consisting of isododecane and isohexadecane.

17. Composition according to claim 16, in which the at least one volatile non-silicone oil is isododecane.

18. Composition according to claim 1, in which the organogelling agent comprises at least one compound chosen from:
N,N'-bis(dodecanoyl)-1,2-diaminocyclohexane,
N,N'-bis(dodecanoyl)-1,3-diaminocyclohexane,
N,N'-bis(dodecanoyl)-1,4-diaminocyclohexane,
N,N'-bis(dodecanoyl)-1,2-ethylenediamine,
N,N'-bis(dodecanoyl)-1-methyl-1,2-ethylenediamine,
N,N'-bis(dodecanoyl)-1,3-diaminopropane,
N,N'-bis(dodecanoyl)-1,12-diaminododecane, and
N,N'-bis(dodecanoyl)-3,4-diaminotoluene.

19. Composition according to claim 1, in which the organogelling agent comprises at least one compound chosen from the compounds of formula (XV):

in which the groups $R^{48}$, which are identical or different, are chosen from a hydrogen atom and saturated, linear and branched hydrocarbon chains, the said hydrocarbon chains containing from 1 to 6 carbon atoms;
the groups Z, which are identical or different, each represent a group chosen from the following groups: —CO—S—$R^{49}$; —CO—NHR$^{49}$; —NH—COR$^{49}$ and —S—COR$^{49}$; in which the groups $R^{49}$, which may be identical or different, are chosen from:
a hydrogen atom,
aryl groups,
aralkyl groups, and
saturated hydrocarbon chains chosen from linear, branched and cyclic hydrocarbon chains, containing from 1 to carbon atoms, optionally substituted with at least one group chosen from aryl, ester, amide and urethane groups; and/or optionally comprising at least one heteroatom chosen from O, S and N; and/or optionally substituted with at least one fluorine atom and/or one hydroxyl radical.

20. Composition according to claim 19, in which in the formula (XV), each $R^{48}$ is a hydrogen atom.

21. Composition according to claim 19, in which in the formula (XV), each Z is chosen from the groups CONHR$^{49}$ and NH—COR$^{49}$.

22. Composition according to claim 19, in which in the formula (XV), $R^{49}$ is chosen from aryl groups; aralkyl groups in which the alkyl portion is a linear or branched alkyl chain comprising 12 to 16 carbon atoms; and linear and branched $C_{11}$-$C_{18}$ alkyl chains.

23. Composition according to claim 19, in which the organogelling agent is chosen from:
cis-1,3,5-tris(dodecylaminocarbonyl)cyclohexane,
cis-1,3,5-tris(octadecylaminocarbonyl)cyclohexane,
cis-1,3,5-tris[N-(3,7-dimethyloctyl)aminocarbonyl]-cyclohexane,
trans-1,3,5-trimethyl-1,3,5-tris(dodecylaminocarbonyl) cyclohexane, and
trans-1,3,5-trimethyl-1,3,5-tris(octadecylaminocarbonyl)-cyclohexane.

24. Composition according to claim 1, in which the organogelling agent is present in a quantity ranging from 0.1% to 80% by weight relative to the total weight of the composition.

25. Composition according to claim 1, in which the organogelling agent is present in a quantity ranging from 0.5% to 60% by weight relative to the total weight of the composition.

26. Composition according to claim 1, in which the polymer/non-polymeric organogelling agent mass ratio is in the range from 20 to 0.15.

27. Composition according to claim 1, wherein the composition further comprises at least one cosmetic or dermatological active agent.

28. Composition according to claim 1, wherein the active agent is chosen from essential oils, vitamins, moisturizers, sunscreens, cicatrizing agents and ceramides.

29. Composition according to claim 1, wherein comprises at least one additive chosen from dyes that are soluble in polyols or in the fatty phase, antioxidants, essential oils, preserving agents, perfumes, liposoluble polymers, liquid-fatty-phase gelling agents, waxes, gums, resins, surfactants, water, emollients, moisturizers, vitamins, liquid lanolin, essential fatty acids, lipophilic sunscreens or sunscreens that are soluble in polyols, lipid vesicles, and mixtures thereof.

30. Composition according to claim 1, wherein the composition further comprises an amphiphilic compound which is liquid at room temperature, having a hydrophilic/lipophilic balance value of less than 12.

31. Composition according to claim 1, wherein the composition comprises at least one colouring matter other than a pigment.

32. Composition according to claim 1, in the form of an anhydrous stick.

33. Composition according to claim 1, in the form of a make-up.

34. Composition according to claim 33, wherein the composition is self-supporting.

35. Composition according to claim 1, in the form of a lipstick.

36. Composition according to claim 1, in the form of a cake mascara, an eyeliner, a foundation, a lipstick, a blusher, a make-up-removing or deodorant product, a make-up product for the body, an eyeshadow or a face powder, or a concealer product.

37. A method of making up a keratinous material comprising applying the composition of claim 1 to the keratinous material.

38. Composition according to claim 1, in which the organogelling agent comprises at least one sterol derivative selected from the group consisting of lanosterol, dihydrolanosterol, and cholesterol esters.

39. Composition according to claim 1, in which the organogelling agent comprises at least trans-(1R,2R)-bis(undecylcarbonylamino)cyclohexane of formula:

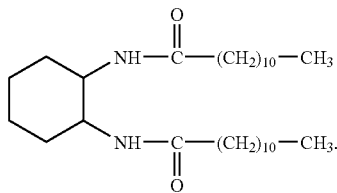

40. Composition according to claim 1, in which the organogelling agent comprises at least one compound chosen from diamides of formula (XXV) or (XXVI):

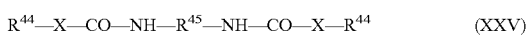

or

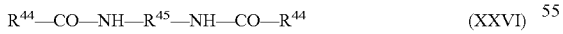

in which the groups $R^{44}$, which may be identical or different, represent a saturated, linear or branched $C_8$-$C_{60}$ hydrocarbon chain, the group(s) $R^{44}$ optionally comprising a hydroxyl group or at least one heteroatom such as N, O, S or Si, $R^{45}$ is a hydrocarbon-based group chosen from linear, branched and cyclic $C_1$ to $C_{50}$ groups and $C_5$ to $C_8$ arylene groups optionally substituted with one or more $C_1$-$C_4$ alkyl groups, and X represents —O— or —NH—, and mixtures thereof.

41. A method of making a composition comprising combining at least one nylon 611/dimethicone copolymer with a liquid continuous fatty phase comprising at least one volatile silicone oil and at least one-volatile non-silicone oil, the liquid fatty phase comprising silicone oil(s) having a flash point equal to or greater than 40° C. and greater than the softening point of the and an organogelling agent, wherein the organogelling agent is selected from the group consisting of:

(1) —N,N'-bis(dodecanoyl)-1,2-diaminocyclohexane,
(2) —N,N'-bis(dodecanoyl)-1,3-diaminocyclohexane,
(3) —N,N'-bis(dodecanoyl)-1,4-diaminocyclohexane,
(4) —N,N'-bis(dodecanoyl)-1,2-ethylenediamine,
(5) —N,N'-bis(dodecanoyl)-1-methyl-1,2-ethylenediamine,
(6) —N,N'-bis(dodecanoyl)-1,3-diaminopropane,
(7) —N,N'-bis(dodecanoyl)-1,12-diaminododecane,
(8) —N,N'-bis(dodecanoyl)-3,4-diaminotoluene,
(9) —at least one compound chosen from the compounds of formula (XV):

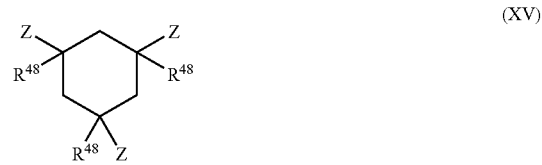

in which the groups $R^{48}$, which are identical or different, are chosen from a hydrogen atom and saturated, linear and branched hydrocarbon chains, the said hydrocarbon chains containing from 1 to 6 carbon atoms;
the groups Z, which are identical or different, each represent a group chosen from the following groups: —CO—S—$R^{49}$; —CO—NHR$^{49}$; —NH—COR$^{49}$ and —S—COR$^{49}$; in which the groups $R^{49}$, which may be identical or different, are chosen from:
a hydrogen atom,
aryl groups,
aralkyl groups, and
saturated hydrocarbon chains chosen from linear, branched and cyclic hydrocarbon chains, containing from 1 to carbon atoms, optionally substituted with at least one group chosen from aryl, ester, amide and urethane groups; and/or optionally comprising at least one heteroatom chosen from O, S and N; and/or optionally substituted with at least one fluorine atom and/or one hydroxyl radical,

(10) —sterol derivatives selected from the group consisting of lanosterol, dihydrolanosterol, and cholesterol esters,

(11) —diamides of formula (XXV) or (XXVI):

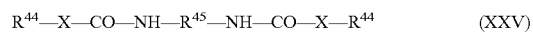

or

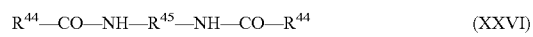

in which the groups $R^{44}$, which may be identical or different, represent a saturated, linear or branched $C_8$-$C_{60}$ hydrocarbon chain, the group(s) $R^{44}$ optionally comprising a hydroxyl group or at least one heteroatom such as N, O, S or Si, $R^{45}$ is a hydrocarbon-based group chosen from linear, branched and cyclic $C_1$ to $C_{50}$ groups and $C_5$ to $C_8$ arylene groups optionally substituted with one or more $C_1$-$C_4$ alkyl grow s, and X represents —O— or —NH—, and mixtures thereof,

(12) —trans-(1R,2R)-bis(undecylcarbonylamino)cyclohexane of formula:

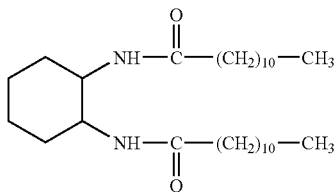

and at least one pigment in an amount sufficient to provide a coloring effect to keratin materials upon application, to form a composition which is in the form of a self-supporting solid with a hardness ranging from 20 to 2 000 gf.

42. Care and/or make-up cosmetic composition comprising a liquid fatty phase comprising at least one volatile silicone oil and at least one volatile non-silicone oil, structured with a gelling system comprising:
1) at least one nylon 611/dimethicone copolymer,
2) at least one non-polymeric organogelling agent, wherein the organogelling agent is selected from the group consisting of:
N,N'-bis(dodecanoyl)-1,2-diaminocyclohexane,
N,N'-bis(dodecanoyl)-1,3-diaminocyclohexane,
N,N'-bis(dodecanoyl)-1,4-diaminocyclohexane,
N,N'-bis(dodecanoyl)-1,2-ethylenediamine,
N,N'-bis(dodecanoyl)-1-methyl-1,2-ethylenediamine,
N,N'-bis(dodecanoyl)-1,3-diaminopropane,
N,N'-bis(dodecanoyl)-1,12-diaminododecane,
N,N'-bis(dodecanoyl)-3,4-diaminotoluene,
at least one compound chosen from the compounds of formula (XV):

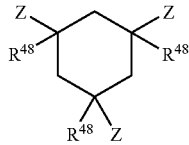

(XV)

in which the groups $R^{48}$, which are identical or different, are chosen from a hydrogen atom and saturated, linear and branched hydrocarbon chains, the said hydrocarbon chains containing from 1 to 6 carbon atoms;

the groups Z, which are identical or different, each represent a group chosen from the following groups: —CO—S—$R^{49}$; —CO—NH$R^{49}$; —NH—CO$R^{49}$ and —S—CO$R^{49}$; in which the groups $R^{49}$, which may be identical or different, are chosen from:
a hydrogen atom,
aryl groups,
aralkyl groups, and
saturated hydrocarbon chains chosen from linear, branched and cyclic hydrocarbon chains, containing from 1 to carbon atoms, optionally substituted with at least one group chosen from aryl, ester, amide and urethane groups; and/or optionally comprising at least one heteroatom chosen from O, S and N; and/or optionally substituted with at least one fluorine atom and/or one hydroxyl radical, sterol derivatives selected from the group consisting of lanosterol, dihydrolanosterol, and cholesterol esters, and trans-(1R,2R)-bis(undecylcarbonylamino)cyclohexane of formula:

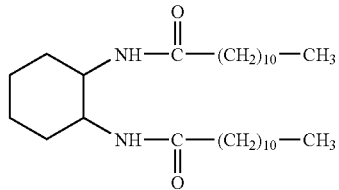

the liquid fatty phase and the gelling system forming a physiologically acceptable medium, and
3) at least one pigment in an amount sufficient to provide a coloring effect to keratin materials upon application.

\* \* \* \* \*

UNITED STATES PATENT AND TRADEMARK OFFICE
CERTIFICATE OF CORRECTION

PATENT NO. : 7,820,146 B2
APPLICATION NO. : 10/517390
DATED : October 26, 2010
INVENTOR(S) : Veronique Ferrari et al.

It is certified that error appears in the above-identified patent and that said Letters Patent is hereby corrected as shown below:

Column 50, line 26, insert --22-- before "carbon".

Column 52, line 25, insert --22-- before "carbon".

Column 54, line 43, insert --22-- before "carbon";

line 66, "alkyl grow" should read --alkyl groups--.

Column 56, line 18, insert --22-- before "carbon".

Signed and Sealed this
Eighteenth Day of January, 2011

David J. Kappos
*Director of the United States Patent and Trademark Office*